(12) United States Patent
Chiou et al.

(10) Patent No.: US 10,307,507 B2
(45) Date of Patent: Jun. 4, 2019

(54) HYDROCOLLOID WOUND DRESSINGS WITH INCREASED WVTR

(71) Applicant: 3M INNOVATIVE PROPERTIES COMPANY, St. Paul, MN (US)

(72) Inventors: Herbert C. Chiou, Coral Springs, FL (US); Hae-Seung Lee, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 708 days.

(21) Appl. No.: 14/775,084

(22) PCT Filed: Mar. 11, 2014

(86) PCT No.: PCT/US2014/023557
§ 371 (c)(1),
(2) Date: Sep. 11, 2015

(87) PCT Pub. No.: WO2014/159419
PCT Pub. Date: Oct. 2, 2014

(65) Prior Publication Data
US 2016/0015851 A1     Jan. 21, 2016

Related U.S. Application Data

(60) Provisional application No. 61/784,367, filed on Mar. 14, 2013.

(51) Int. Cl.
*A61L 15/58* (2006.01)
*A61L 24/04* (2006.01)
(Continued)

(52) U.S. Cl.
CPC ........... *A61L 15/585* (2013.01); *A61L 15/225* (2013.01); *A61L 15/60* (2013.01); *A61L 24/0031* (2013.01);
(Continued)

(58) Field of Classification Search
None
See application file for complete search history.

(56) References Cited

U.S. PATENT DOCUMENTS 4,231,369 A   11/1980   Sorensen
4,477,325 A   10/1984   Osburn
(Continued)

FOREIGN PATENT DOCUMENTS

WO   WO 2010-129199   11/2010
WO   WO 2011-057240   5/2011

OTHER PUBLICATIONS

Tsukada, "The pH Changes of Pressure Ulcers Related to the Healing Process of Wounds", WOUNDS: A Compendium of Clinical Research and Practice, 1992, vol. 4, No. 1, p. 16-20.
(Continued)

*Primary Examiner* — Bethany P Barham
*Assistant Examiner* — Dominic Lazaro
(74) *Attorney, Agent, or Firm* — Ann K. Gallagher

(57) ABSTRACT

Hydrocolloid compositions, wound dressings, methods of using such compositions and such wound dressings, and methods of forming such hydrocolloid compositions, wherein the hydrocolloid compositions include a hydrophobic, unsaturated, elastomeric polymer; a hydrocolloid absorbent; and a hydrophilic polymer including an unsaturated polymer backbone having polyalkylene ether groups bonded thereto.

19 Claims, 5 Drawing Sheets

(51) Int. Cl.

| | | |
|---|---|---|
| *C09J 147/00* | (2006.01) | |
| *A61L 15/22* | (2006.01) | |
| *C09J 179/02* | (2006.01) | |
| *A61L 24/00* | (2006.01) | |
| *A61L 15/60* | (2006.01) | |
| *C09J 123/20* | (2006.01) | |
| *C08L 1/28* | (2006.01) | |
| *C08L 9/00* | (2006.01) | |
| *C08L 87/00* | (2006.01) | |
| *C08G 81/02* | (2006.01) | |

(52) U.S. Cl.
CPC .............. *A61L 24/043* (2013.01); *C08L 1/286* (2013.01); *C08L 9/00* (2013.01); *C08L 87/00* (2013.01); *C09J 123/20* (2013.01); *C09J 147/00* (2013.01); *C09J 179/02* (2013.01); *A61L 2400/14* (2013.01); *A61L 2420/06* (2013.01); *C08G 81/025* (2013.01)

(56) References Cited

U.S. PATENT DOCUMENTS

| | | | |
|---|---|---|---|
| 4,539,256 A | 9/1985 | Shipman | |
| 4,551,490 A | 11/1985 | Doyle | |
| 4,598,004 A | 7/1986 | Heinecke | |
| 4,738,257 A | 4/1988 | Meyer | |
| 4,952,618 A | 8/1990 | Olsen | |
| 5,147,925 A * | 9/1992 | Pears | C08G 18/0804 524/589 |
| 5,468,821 A | 11/1995 | Lucast | |
| 5,622,711 A | 4/1997 | Chen | |
| 5,633,010 A | 5/1997 | Chen | |
| 5,648,166 A | 7/1997 | Dunshee | |
| 6,264,976 B1 | 7/2001 | Heinecke | |
| 6,375,977 B1 | 4/2002 | Auguste et al. | |
| 6,436,432 B2 | 8/2002 | Heinecke | |
| 6,497,949 B1 | 12/2002 | Hyde | |
| 6,534,561 B1 | 3/2003 | Corzani et al. | |
| 6,583,220 B1 | 6/2003 | Lipman | |
| 6,780,484 B2 | 8/2004 | Kobe | |
| 7,659,323 B2 | 2/2010 | Lewandowski | |
| 7,910,790 B2 | 3/2011 | Johnston | |
| 8,076,528 B2 | 12/2011 | Lam | |
| 8,871,993 B2 | 10/2014 | Buus et al. | |
| 9,249,343 B2 | 2/2016 | Buus et al. | |
| 2003/0125680 A1 | 7/2003 | Ding | |
| 2010/0030179 A1 | 2/2010 | Burton | |
| 2011/0166492 A1 | 7/2011 | Holm | |
| 2011/0319847 A1 | 12/2011 | McKiernan et al. | |
| 2014/0371692 A1 | 12/2014 | Cleary et al. | |

OTHER PUBLICATIONS

International Search Report for PCT International Application No. PCT/US2014/23557 dated Aug. 19, 2014, 2 pages.

* cited by examiner

HYDROCOLLOID WOUND DRESSINGS WITH INCREASED WVTR

CROSS REFERENCE TO RELATED APPLICATIONS

This application is a national stage filing under 35 U.S.C. 371 of PCT/US2014/023557, filed Mar. 11, 2014, which claims priority to U.S. Application No. 61/784,367, filed Mar. 14, 2013, the disclosures of which are incorporated by reference in their entirety herein.

BACKGROUND

This disclosure relates to hydrocolloid compositions, having a variety of medical uses, particularly in the field of wound dressings, ostomy care, and prosthesis application. In addition, this disclosure also relates to wound dressings that include such hydrocolloid compositions, methods of using such compositions, particularly in wound dressings, and to methods of forming such hydrocolloid compositions.

Hydrocolloid compositions, particularly adhesive compositions, as well as wound dressings and ostomy products formed from these hydrocolloid compositions, have been known for many years. Typically, these compositions include a blend of a polymer matrix, such as a rubbery elastomer like polyisobutylene, in combination with one or more water-soluble or water-swellable hydrocolloids, such as a dry powdered mixture of pectin, gelatin and carboxymethylcellulose.

When included in a wound dressing or ostomy seal, the adhesive composition is usually coated on at least one surface of a water-insoluble film. A major problem with many conventional hydrocolloid compositions is their susceptibility to breakdown upon exposure to wound exudate and body fluids (i.e., their lack of structural integrity after being hydrated). When the compositions are used as skin barriers, e.g., around stomas, some absorption of fluid is desirable, but excessive swelling causes the composition to lose its moisture seal with the skin. Leakage occurs and the barrier must be replaced more often than is desirable. Thus, hydrocolloid compositions that use hydrophobic polymers have been developed.

SUMMARY

A more hydrophilic hydrocolloid composition, however, than conventional hydrophobic hydrocolloids is desired to allow for more facile moisture or fluid transportation to the hydrocolloid particles themselves or vapour migrating through the material. Thus, it would be desirable to provide hydrocolloid compositions having improved (i.e., increased) moisture vapor transmission rate (MVTR) (i.e., water vapor transmission rate (WVTR)).

This present disclosure provides hydrocolloid compositions, wound dressings, methods of using such compositions and such wound dressings, and to methods of forming such hydrocolloid compositions. The hydrocolloid compositions are preferably adhesives, particularly pressure sensitive adhesives.

Such hydrocolloid compositions, and products that incorporate such compositions, have increased water vapor transmission rates (WVTR) (i.e., moisture vapor transmission rate or MVTR). Such hydrocolloid compositions having increased WVTR could be used for medical applications over a wound (e.g., cut, insect bite, acne, or cold-sore), for example. It could also be used as a gasket for negative pressure wound therapy, in ostomy care, and in prosthesis applications.

The component that is used to increase the WVTR of a hydrocolloid composition is a hydrophilic polymer that includes an unsaturated polymer backbone having polyalkylene ether groups bonded thereto. Such polymer may be referred to herein as a WVTR-modifying component.

In certain embodiments, the present disclosure provides a hydrocolloid composition that includes: a hydrophobic, unsaturated, elastomeric polymer; a hydrocolloid absorbent; and a hydrophilic polymer including an unsaturated polymer backbone having polyalkylene ether groups bonded thereto. Such composition is typically crosslinked. That is, in a product useful for medical applications, the hydrophobic and hydrophilic polymers are crosslinked to provide the composition with a crosslinked matrix. Even when crosslinked, the polymers are still typically partially unsaturated.

In certain embodiments, the present disclosure provides a hydrocolloid composition that is in the form of an adhesive, particularly a pressure sensitive adhesive (PSA). Often in this case, low molecular weight, high $T_g$ resin polymers (tackifiers) or low molecular weight, low $T_g$ polymers (plasticizers) are often used to modulate the $T_g$ and modulus into an optimal PSA range.

In certain embodiments, a hydrocolloid composition of the present disclosure includes: a hydrophobic, unsaturated, elastomeric homopolymer; a tackifier; a hydrocolloid absorbent selected from the group of a natural hydrocolloid, a semi-synthetic hydrocolloid, a synthetic hydrocolloid, and combinations thereof; and a hydrophilic polymer including an unsaturated polymer backbone having polyalkylene ether groups bonded thereto; wherein the hydrophobic and hydrophilic polymers are crosslinked by 5-200 kGy gamma radiation to provide an adhesive composition with a crosslinked matrix. Even when crosslinked, the polymers are still typically partially unsaturated.

In certain embodiments, a hydrocolloid composition of the present disclosure includes: 20-50 wt-% of a hydrophobic, unsaturated, elastomeric homopolymer; 5-60 wt-% of a hydrocolloid absorbent; and 0.5-20 wt-% of a hydrophilic polymer including an unsaturated polymer backbone having polyalkylene ether groups bonded thereto; wherein the hydrocolloid composition is in the form of a pressure sensitive adhesive; and wherein the hydrophilic polymer is present in an amount that increases the WVTR of the hydrocolloid composition relative to the same hydrocolloid composition without the hydrophilic polymer.

In certain embodiments, the present disclosure provides a wound dressing that includes a hydrocolloid composition as described herein coated on a surface of a moisture vapor permeable backing. In certain embodiments, the backing further includes a release coating coated on the surface of the backing opposite the surface coated with the hydrocolloid composition.

In certain embodiments, the present disclosure provides an ostomy pouch that includes a hydrocolloid composition described herein.

The present disclosure also provides methods, such as methods of using and methods of making compositions described herein.

For example, in one embodiment, the present disclosure provides a method of treating a wound that includes applying to the wound a hydrocolloid composition as disclosed herein or a wound dressing disclosed herein.

In another embodiment, the present disclosure provides a method of forming a hydrocolloid composition, wherein the method includes: compounding a mixture that includes: a hydrophobic, unsaturated, elastomeric polymer; a hydrocolloid absorbent; and a hydrophilic polymer including an unsaturated polymer backbone having polyalkylene ether groups bonded thereto; and irradiating the mixture with radiation sufficient to crosslink the hydrophobic and hydrophilic polymers and form a composition with a crosslinked matrix that includes partial unsaturation.

In another embodiment, the present disclosure provides a method of forming a hydrocolloid composition, wherein the method includes: compounding a mixture that includes: a first hydrophobic, unsaturated, elastomeric polymer; a hydrocolloid absorbent; a second hydrophobic, unsaturated polymer; and a hydrophilic polyalkylene oxide-containing compound; and irradiating the mixture with radiation sufficient to crosslink the hydrophobic and hydrophilic polymers and form a composition with a crosslinked matrix that includes partial unsaturation.

The present disclosure also provides a hydrophilic polymer that includes an unsaturated polymer backbone having pendant polyalkylene ether groups bonded thereto.

A hydrophobic, unsaturated, elastomeric polymer is used as the hydrophobic base polymer of the hydrocolloid compositions of the present disclosure.

In this context, a "hydrophobic" polymer refers to an organic polymer, typically an olefin polymer, that is substantially water insoluble at room temperature (e.g., demonstrates a water uptake is less than 5 wt-%).

In this context, "unsaturated" refers to unsaturated carbon-carbon double bonds in the polymer backbone and/or branched side chains.

A hydrophilic polymer including an unsaturated polymer backbone having polyalkylene ether groups bonded thereto is used as the WVTR-modifying component of the hydrocolloid compositions of the present disclosure.

In this context, a "hydrophilic" polymer refers to an organic polymer that is substantially water soluble or water swellable at room temperature (e.g., demonstrates a water uptake of greater than 10 wt-%).

In this context, "backbone" refers to the main chain of a polymer.

In this context, "unsaturated" refers to unsaturated carbon-carbon double bonds in the polymer backbone.

Herein, "moisture vapor transmission rate" (MVTR), also referred to as "water vapor transmission rate" (WVTR), is a measure of the passage of water vapor through a substance.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the term "room temperature" refers to a temperature of about 20° C. to about 25° C. or about 22° C. to about 25° C.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The disclosure may be further illustrated by reference to the accompanying Drawings wherein.

DETAILED DESCRIPTION OF EXEMPLARY EMBODIMENTS

Figure 1:
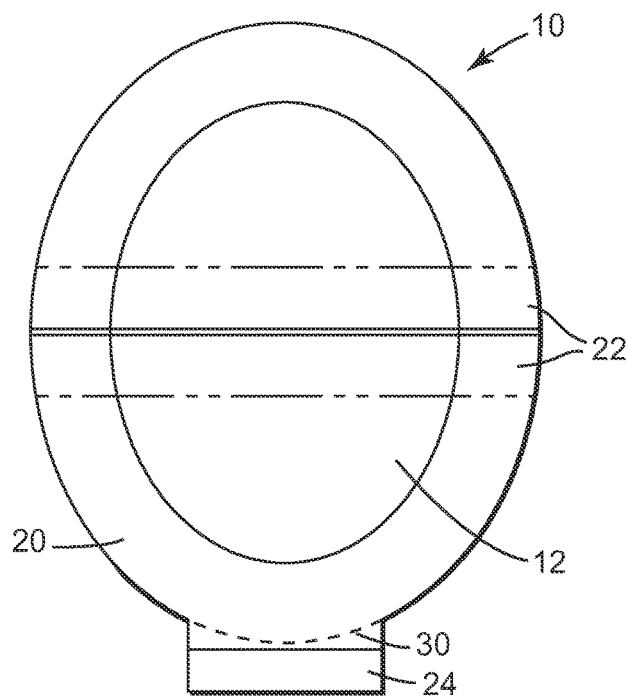
FIG. 1 is a top view of a wound dressing incorporating the hydrocolloid composition of the present disclosure.

This present disclosure provides hydrocolloid compositions, wound dressings, methods of using such compositions and such wound dressings, and to methods of forming such hydrocolloid compositions. The hydrocolloid compositions are preferably adhesives, particularly pressure sensitive adhesives.

Such hydrocolloid compositions, and products incorporating them, have increased water vapor transmission rates. By increasing the WVTR, the hydrocolloid compositions of the present disclosure may potentially migrate moisture that is normally generated by the body through the dressing while allowing the hydrocolloid to capture exudate from the wound.

In certain embodiments, the present disclosure provides a hydrocolloid composition that is in the form of an adhesive, particularly a pressure sensitive adhesive.

The component that is used to increase the WVTR of a hydrocolloid composition is a hydrophilic polymer that includes an unsaturated polymer backbone having polyalkylene ether groups bonded thereto. The polyalkylene ether groups are tethered to a polymer backbone, thereby preventing their migration; however, the level of WVTR is significantly higher than would be expected by merely immobilizing or incorporating the polyalkylene ether groups. Although not wishing to be bound by theory, it is believed that the tethered polyalkylene ether groups are attracted to each other and form pathways for water vapor to migrate through the matrix. Also, the unsaturated polymer backbone of the hydrophilic polymer, which is derived from a hydrophobic polymer, is believed to provide better compatibility between the hydrophilic polymer and the hydrophobic, unsaturated, elastomeric polymer. Whatever the mechanism of action might be, significantly, the level of WVTR can be controlled (i.e., adjusted as desired) while keeping the total concentration of additives constant.

Hydrocolloid compositions including a WVTR-modifying material of the present disclosure can retain, at least to an acceptable level, one or more of desired adhesive performance characteristics, including adjustable absorbency, high shear holding power, good adhesion to skin, good cohesive strength, good edge adhesion, reduced adhesive cold-flow, and reduced adhesive residues. The performance factors, and the precise effects of the WVTR-modifying material, depend on the exact composition of the materials used.

The hydrophilic polymers as described herein can be incorporated into a variety of conventional hydrocolloid compositions to increase the WVTR of such conventional compositions. Exemplary such conventional compositions include those used in commercially available products, such as DUODERM EXTRA-THIN wound dressing (a product of Convatec; Squibb and Sons, Inc., Princeton, N.J., believed to be a KRATON-based composition under U.S. Pat. No. 4,551,490), TEGASORB wound dressing (a product of 3M Company, St. Paul, Minn., a polyisobutylene-based composition under U.S. Pat. No. 4,952,618), RESTORE wound dressing (a product of Hollister, Inc., Libertyville, Ill., believed to be an ethylene vinyl acetate (EVA)-based composition under U.S. Pat. Nos. 4,477,325 and 4,738,257), and COMFEEL wound dressing (a product of Coloplast International, Espergaerde, Denmark, believed to be a KRATON-based composition under U.S. Pat. No. 4,231,369).

In certain embodiments, hydrocolloid compositions of the present disclosure are prepared from three basic ingredients: (1) a hydrophobic, unsaturated, elastomeric polymer; (2) a hydrocolloid absorbent; and (3) a hydrophilic polymer including an unsaturated polymer backbone having polyalkylene ether groups bonded thereto.

A hydrophobic, unsaturated, elastomeric polymer is used as the hydrophobic base polymer of the hydrocolloid composition. It can also be used as the backbone for the hydrophilic polymer. That is, typically, such hydrophilic polymer is formed from a hydrophobic, unsaturated, elastomeric polymer (although an elastomeric polymer is not required) and a hydrophilic polyalkylene oxide-containing compound. Herein, when used as the base polymer of the hydrocolloid composition, it is referred to as the "first" hydrophobic, unsaturated, elastomeric polymer, and when used to prepare the hydrophilic polymer, it is referred to as the "second" hydrophobic, unsaturated, (optionally, elastomeric) polymer. In certain embodiments, the second hydrophobic, unsaturated, polymer used to prepare the hydrophilic polymer can be the same as the first hydrophobic, unsaturated, elastomeric polymer. Alternatively, the second polymer can include functional groups, e.g., epoxy groups and groups other than the backbone C=C bonds, that form the sites of attachment for the grafted polyether groups.

Hydrophilic Polymers

Hydrophilic polymers of the present disclosure include an unsaturated polymer backbone having polyalkylene ether groups bonded thereto. Accordingly, such groups are pendant groups. The polyalkylene ether groups can also be referred to as poly(alkylene oxide) groups, and are hydrophilic. Such groups typically include ethylene oxide units and optionally co-polymerized propylene oxide units. Typically, the polyalkylene ether groups include at least 70 weight percent (wt-%) ethylene oxide units, based on the total weight of the polyalkylene oxide-containing compound from which the pendant groups are obtained.

In certain embodiments, the unsaturated polymer backbone typically accounts for at least 20 wt-%, and often up to 95 wt-%, of the hydrophilic polymer. In certain embodiments, the hydrophilic polyalkylene ether groups account for at least 5 wt-%, and often up to 80 wt-%, of the hydrophilic polymer.

The pendant polyalkylene ether groups are derived from a hydrophilic polyalkylene oxide-containing compound. In this context, "hydrophilic" has the same definition as that provided for the hydrophilic polymer that includes the unsaturated polymer backbone. In certain embodiments, the hydrophilic polyalkylene oxide-containing compound includes ethylene oxide units and optionally co-polymerized propylene oxide units. Typically, the hydrophilic polyalkylene oxide-containing compound (from which the pendant groups of the hydrophilic polymer are derived) includes at least 70 wt-% ethylene oxide units, based on the weight of the hydrophilic polyalkylene oxide-containing compound.

In certain embodiments, the hydrophilic polyalkylene oxide-containing compound includes "PEG" or polyethylene glycol units. As used herein, this is meant to encompass any water-soluble poly(ethylene oxide)-containing compound. Most typically, PEGs (i.e., PEG-containing compounds) for use in the present disclosure will contain the following structure, $-CH_2CH_2O(CH_2CH_2O)_nCH_2CH_2-$, wherein the terminal groups or actual architecture of the overall PEG moiety may vary. The PEG-containing compounds (and the more general polyalkylene oxide-containing compounds) include poly(ethylene glycol) units (and optional poly(propylene glycol) units) in any of its linear, branched, or multi-arm forms.

Typically, the hydrophilic polymer is derived from a hydrophobic, unsaturated, elastomeric polymer and a hydrophilic polyalkylene oxide-containing compound. Each of these materials includes reactive functionality that provides sites of reaction between such materials. In certain embodiments, the hydrophobic, unsaturated, elastomeric polymer and the hydrophilic polyalkylene oxide-containing compound are reacted in a weight ratio from 7:3 to 3:7.

The hydrophilic polyalkylene oxide-containing compounds include one reactive group that serves as the point of reaction with the polymer that serves as the polymer backbone. Such reactive groups include amine groups, thiol groups, hydroxyl groups and their metal salts, carboxylic acid groups and their metal salts. Examples of such compounds include monofunctional polyetheramines, such as those available under the trade name JEFFAMINE from Huntsman Corp., Woodlands, Tex., e.g., JEFFAMINE M-1000 of the following structure:

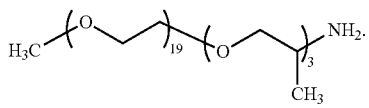

Hydrophilic polyalkylene oxide-containing compounds can be prepared from acrylates, such as $H_3C$—$[OCH_2CH_2]_n$—O—C(O)—CH=$CH_2$, with HS—$CH_2CH_2$—$NH_2$. Depending on the conditions of reaction, various hydrophilic polyalkylene oxide-containing acrylate compounds can be formed (modified ethylene oxide acrylates (A) and/or (B) formed in a solventless reaction carried out at 60-80° C. for 30 minutes to 1 hour; modified ethylene oxide acrylate (C) formed at room temperature in the presence of a photoinitiator (IRGACURE 651) using UV radiation as demonstrate in the Examples Section):

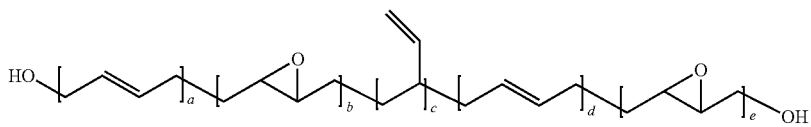

(A)

(B)

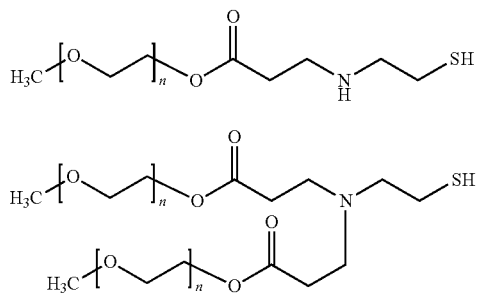

(C)

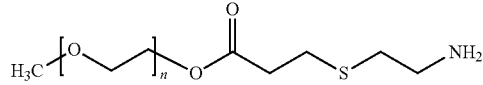

wherein each n is independently 5 to 50, and often 15 to 20.

The hydrophobic, unsaturated polymers that can be used as the backbone to which the polyalkylene oxide groups can be grafted may or may not be elastomeric. They include those elastomeric polymers described herein below for the base polymer of the hydrocolloid composition. They include polyisoprene, polybutadiene, butyl rubber (e.g., isoprene, isobutylene copolymer), halogenated butyl rubber, etc., and combinations thereof. The unsaturation (e.g., C=C bonds) in these polymers provide sites for grafting the polyalkylene oxide groups. Alternatively, such polymers can include reactive sites (other than the C=C bonds) such as epoxy groups and halogen groups. Thus, such hydrophobic, unsaturated, polymers are referred to herein as "optionally functionalized" (herein, this refers to a functional group other than a C=C double bond).

Examples of such functionalized polymers include epoxy-functional polymers such as epoxidized hydroxyl-terminated polybutadiene resin (Poly BD 605E, Cray Valley) of the following structure:

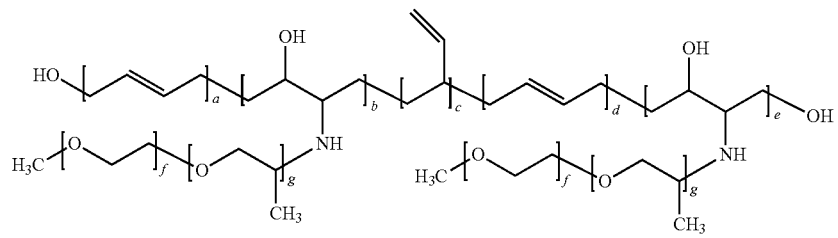

wherein a+b+c+d+e=10-2000 (often 20-30), and the number average molecular weight is typically 500 to 100,000 Daltons.

The representations used herein for the polymers do not necessarily mean that there are blocks of the units within the "a" group or "b" group or "c" group, etc.; rather, these representations refer to the numbers of such units, not that they are all in blocks. Such monomeric units are typically randomly connected.

In one exemplary reaction, epoxidized liquid polybutadiene and monofunctional EO/PO JEFFAMINE M-1000 (in a solventless reaction at 60-70° C. for 0.5-1.0 hour), form the following hydrophilic polymer (an EO/PO-grafted epoxidized polybutadiene):

wherein a+b+c+d+e=10-2000 (often 20-30), g=3, and f=19. This representation does not necessarily mean that there are blocks of ethylene oxide groups that include "f" number of such groups and blocks of propylene oxide groups that include "g" number of such groups. This representation is to simply show that there are pendant chains with "f" and "g" number of ethylene oxide and propylene oxide groups, respectively. Such groups are typically randomly connected.

Similar hydrophilic polymers can be prepared wherein a+b+c+d+e=10-2000 and g+f=5-250, wherein the number of "f" groups (hydrophilic ethylene oxide groups) is greater than the number of "g" groups (hydrophobic propylene oxide groups), and the number average molecular weights range from 200 to 10,000 Daltons.

In another exemplary reaction, epoxidized liquid polybutadiene and the modified ethylene oxide acrylate (C) (in a solventless reaction at 70-80° C. for 0.5-1.0 hour) form the following hydrophilic polymer (a PEG-grafted epoxidized polybutadiene):

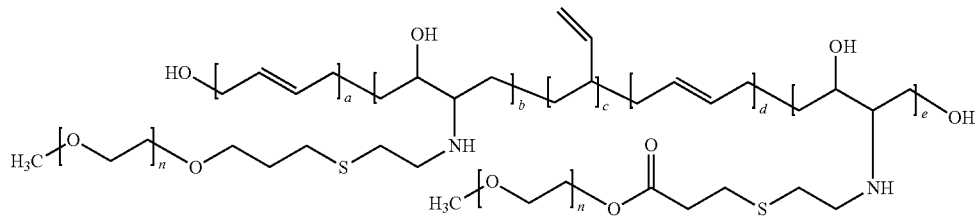

wherein a+b+c+d+e=10-2000 (often 20-30), and each n is independently 5-50 (often 15-20).

In another exemplary reaction, polyisoprene and the modified ethylene oxide acrylate (B) (at room temperature in the presence of a photoinitiator (IRGACURE 651) using UV radiation as demonstrated in the Examples Section) form the following hydrophilic polymer (PEG-grafted polyisoprene):

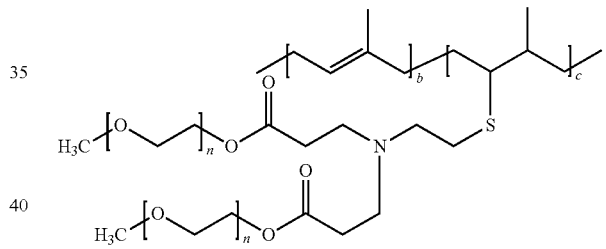

wherein b+c=10-2000 (often 400-450), and each n is independently 5-50 (often 15-20).

In yet another exemplary reaction, polybutylene and the modified ethylene oxide acrylate (B) (at room temperature in the presence of a photoinitiator (IRGACURE 651) using UV radiation) form the following hydrophilic polymer (PEG-grafted polybutadiene):

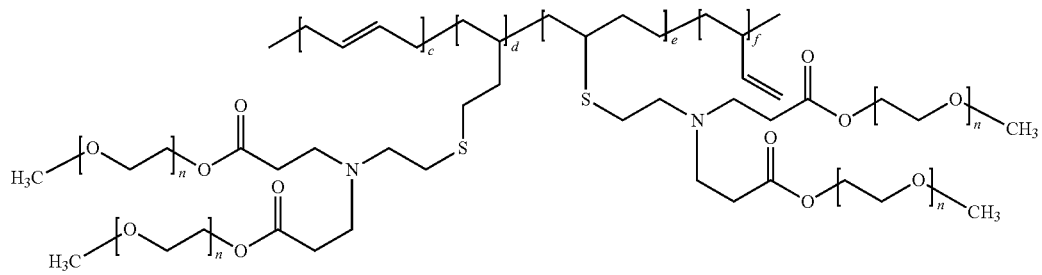

wherein c+d+e+f=10-2000 (often 40-50), and each n is independently 5-50 (often 15-20).

In yet another exemplary reaction, polybutylene and the modified ethylene oxide acrylate (A) (at room temperature in the presence of a photoinitiator (IRGACURE 651) form the following hydrophilic polymer (PEG-grafted polybutadiene):

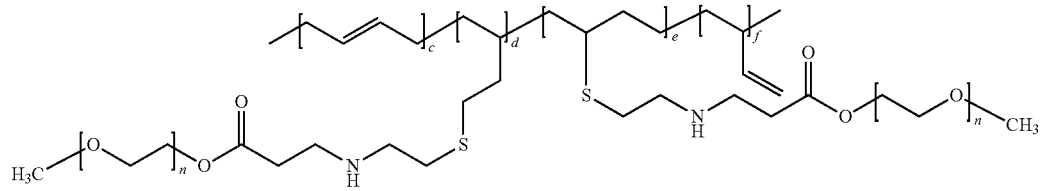

wherein c+d+e+f=10-2000 (often 40-50), and each n is independently 3-50 (often 15-20).

Molecular weights of the polymers that form the backbone of the hydrophilic polymer can vary over a wide range. For example, number average molecular weights can range from at least 200, or at least 500 Daltons, and often up to 100,000 Daltons (when "up to" a number is used, it includes that number). Preferred molecular weights are those that provide a polymer that is flowable at room temperature or processing temperatures (e.g., 80-100° C.).

Molecular weights of the hydrophilic polyalkylene oxide-containing compounds that form the pendant polyalkylene ether groups can vary over a wide range. For example, number average molecular weights can range from 100 to 10,000 Daltons. Preferred molecular weights are those that provide a compound that does not have too high a melting point such that processing is difficult and costly.

Care should be taken when selecting the backbone such that it does not adversely react with the hydrophobic matrix. For example, an epoxidized backbone in an acidic matrix (e.g., one including polymers containing acrylic acid moieties) may not provide acceptable results.

Hydrocolloid Compositions

Hydrocolloid compositions of the present disclosure include at least one hydrophobic, unsaturated, elastomeric polymer, at least one hydrocolloid absorbent, and at least one hydrophilic polymer including an unsaturated polymer backbone having polyalkylene ether groups bonded thereto. Such compositions are typically crosslinked. That is, in a product, particularly one useful for medical applications, the hydrophobic and hydrophilic polymers are crosslinked to provide the composition with a crosslinked matrix. Even when crosslinked, the polymers are still typically partially unsaturated. Such polymers may be crosslinked by bonding polymer chains within a polymer (e.g., within the hydrophobic polymer or within the hydrophilic polymer) or between the different polymers (e.g., between the hydrophobic and hydrophilic polymers).

Typically, hydrocolloid compositions of the present disclosure are prepared by initially combining the basic ingredients (i.e., the at least one hydrophobic, unsaturated, elastomeric polymer (e.g., an aliphatic homopolymer), the at least one hydrocolloid absorbent, and the at least one hydrophilic polymer including an unsaturated polymer backbone having polyalkylene ether groups bonded thereto), and optional ingredients (e.g., at least one tackifier and at least one plasticizer). This mixture of ingredients is exposed to a dose of ionizing radiation which chemically crosslinks the unsaturated groups, thereby yielding high integrity compositions, particularly adhesive compositions, of the present disclosure. While it is preferable to irradiate the ingredients after mixing and forming into a desired shape (e.g., an adhesive sheet), it is possible to irradiate the ingredients prior to mixing and/or forming into a desired shape. However, in such an instance, the complete mixing of the ingredients may be impeded, and the resulting mixture may still need to be exposed to a further dose of radiation to provide the high integrity compositions of the present disclosure.

A hydrophobic, unsaturated, elastomeric polymer is used as the hydrophobic base polymer of the hydrocolloid composition. It is one of the main components of a hydrocolloid composition and typically functions as a matrix to hold everything together.

While potentially any degree of unsaturation may serve to form the compositions of the present disclosure, the hydrophobic unsaturated polymer preferably exhibits at least fifty mole percent (50%) unsaturation, and more preferably at least ninety mole percent (90%) unsaturation. In an especially preferred embodiment, the hydrophobic unsaturated polymer exhibits virtually one hundred mole percent (100%) unsaturation, i.e., essentially 100% unsaturated double bonds per monomer unit of the polymer.

In certain embodiments, the hydrophobic, unsaturated, elastomeric polymer is typically a homopolymer, and preferably an aliphatic homopolymer. Exemplary such polymers can include either a straight-chain unsaturated aliphatic homopolymer, a branched unsaturated aliphatic homopolymer, or a combination thereof. In addition, the hydrophobic unsaturated aliphatic homopolymer can be substituted along its polymer chain with another moiety, such as chlorine, fluorine, or a lower alkyl, and still be considered to fall within the scope of the present disclosure.

Nonlimiting examples of suitable hydrophobic, unsaturated, elastomeric polymers include polyisoprene, polybutadiene, butyl rubber (e.g., isoprene, isobutylene copolymer), halogenated butyl rubber, etc., and combinations thereof. For certain embodiments, polyisoprene is particularly preferred. Polyisoprene is commercially available from a number of sources, including Goodyear Chemical Co., Akron, Ohio, under the NATSYN trade name, including NATSYN Resin Nos. 2200, 2205, and 2210.

One or more hydrophobic, unsaturated, elastomeric polymers are typically included within the hydrocolloid composition in an amount of at least 20 percent by weight (wt-%) of the total weight of the hydrocolloid composition. One or more hydrophobic, unsaturated, elastomeric polymers are typically included within the hydrocolloid composition in an amount of up to 50 percent by weight (wt-%) of the total weight of the hydrocolloid composition. For wound dressing applications, it can be desirable to limit the amount of hydrophobic, unsaturated, elastomeric polymer present, in order to maximize the level of hydrocolloid, thereby achieving maximum fluid absorbency. Thus, when forming wound dressings, from 25 weight percent to 35 weight percent of the hydrophobic, unsaturated, elastomeric polymer is typically employed. Conversely, when formulating an adhesive composition for an ostomy skin barrier and/or application of prostheses, maximum hold and minimal absorbency is typically desired. Thus, adhesive compositions of the present disclosure that are formulated for ostomy and/or prosthesis attachment typically include from 35 weight percent to 45 weight percent of the hydrophobic, unsaturated, elastomeric polymer.

The hydrophilic polymer used in hydrocolloid compositions of the present disclosure are those described above. They include an unsaturated polymer backbone having polyalkylene ether groups bonded thereto. The hydrophilic polymer is present in a hydrocolloid composition of the present disclosure in an amount that increases the WVTR of the hydrocolloid composition, (preferably by at least 50 percent (%), or by at least 100% (i.e., 2×), or by at least 200%) relative to the same hydrocolloid composition without the hydrophilic polymer.

One or more hydrophilic polymers are typically included within the hydrocolloid composition in an amount of at least 0.5 percent by weight of the total weight of the hydrocolloid composition. One or more hydrophilic polymers are typically included within the hydrocolloid composition in an amount of up to 20 percent by weight (wt-%) of the total weight of the hydrocolloid composition.

Hydrocolloid absorbents used in the hydrocolloid compositions of the present disclosure are those conventionally used in hydrocolloid compositions, particularly hydrocolloid adhesive compositions.

Exemplary hydrocolloid absorbents include a natural hydrocolloid, such as pectin, gelatin, or carboxymethylcellulose (CMC) (e.g., that available from Aqualon Corp., Wilmington, Del.), a semi-synthetic hydrocolloid, such as crosslinked carboxymethylcellulose (X-link CMC) (e.g., that available under the trade name Ac-Di-Sol from FMC Corp., Philadelphia, Pa.), a synthetic hydrocolloid, such as crosslinked polyacrylic acid (PAA) (e.g., that available under the trade name CARBOPOL No. 974P from B.F. Goodrich, Brecksville, Ohio), or a combination thereof.

One or more hydrocolloid absorbents are typically included within the hydrocolloid composition in an amount of at least 5 percent by weight of the total weight of the hydrocolloid composition. One or more hydrocolloid absorbents are typically included within the hydrocolloid composition in an amount of up to 60 percent by weight (wt-%) of the total weight of the hydrocolloid composition. For wound dressing applications, from 20 weight percent to 40 weight percent of the hydrocolloid absorbent is typically employed. For adhesive compositions of the present disclosure that are formulated for ostomy and/or prosthesis attachment, from 5 weight percent to 20 weight percent of hydrocolloid absorbent is typically employed.

The particular selection of the hydrocolloid absorbents to be used in any one hydrocolloid composition will depend upon the intended use. For example, in preparing a hydrocolloid composition for use with a wound dressing, maximum absorbency without a loss of wet integrity is desired. Thus, a major portion of the hydrocolloid absorbent preferably includes natural hydrocolloids that are water soluble, and provide maximum absorbency. In addition, crosslinked semi-synthetic and synthetic hydrocolloids, which are water swellable, but water insoluble, may also be included in the composition to serve as a filler, and/or to help regulate the swelling of the hydrocolloid composition. Conversely, when formulating ostomy and/or prosthesis adhesives, minimal, if any absorbency, is desired. In such an instance, the cross-linked semi-synthetic and synthetic hydrocolloids would form the majority, if not all, of the hydrocolloid absorbent in the hydrocolloid composition.

Thus, the absorbency of the hydrocolloid compositions of the present disclosure can be adjusted based on the particular need. In general, for ostomy and/or prosthesis adhesives, a hydrocolloid composition will preferably exhibit an absorbency value of less than 50 percent, and more preferably less than 20 percent, after twenty-four hours of exposure to aqueous fluids. On the other hand, when formulating a hydrocolloid composition for use in a wound dressing, a hydrocolloid composition will preferably exhibit an absorbency of at least 50 percent, and more preferably an absorbency of from 100 percent to 500 percent after twenty-four hours of exposure to aqueous fluids. These and other desirable properties of a hydrocolloid composition are described in U.S. Pat. No. 5,622,711. Hydrocolloid compositions of the present disclosure typically possess such properties.

The use of crosslinked polyacrylic acid (PAA) as a hydrocolloid absorbent may provide additional advantages to hydrocolloid, particularly adhesive, compositions according to the present disclosure. Specifically, the acidic nature of PAA lowers the overall acidity of the hydrocolloid, particularly adhesive, compositions of the present disclosure from a pH of 7 to a pH of 5. When such a composition is employed in a wound dressing, the pH of the wound exudate will likewise be lowered. This in turn may lead to promotion of more rapid healing of the wound. See, e.g., K. Tsukada et al., "The pH Changes of Pressure Ulcers Related to the Healing Process of Wounds", 4, WOUNDS: A Compendium of Clinical Research and Practice, 16 (January-February, 1992). In addition, the use of PAA has also been observed to reduce the cold-flow of the adhesive layer of wound dressings formed from the hydrocolloid compositions of the present disclosure As stated above, hydrocolloid compositions of the present disclosure can include optional ingredients, such as one or more tackifiers and/or one or more plasticizers. Often in this case, low molecular weight, high $T_g$ resin polymers (tackifiers) or low molecular weight, low $T_g$ polymers (plasticizers) are often used to modulate the $T_g$ and modulus into an optimal PSA range. Such additives are preferably compatible with the hydrophobic, unsaturated, elastomeric polymer. As used herein, a "compatible" additive refers to an additive (e.g., a tackifier) that is miscible with the hydrophobic, unsaturated, elastomeric polymer, such that when these components are mixed they form a homogeneous phase.

Exemplary tackifiers are those that are typically used in adhesives, particularly pressure sensitive adhesives. Various types of tackifiers include phenol-modified terpenes and rosin esters such as glycerol esters of rosin and pentaerythritol esters of rosin that are available under the trade names NUROZ, NUTAC (Newport Industries), PERMALYN, STAYBELITE, FORAL (Eastman). Also available are hydrocarbon resin tackifiers that typically come from C5 and C9 monomers by products of naphtha cracking and are available under the trade names PICCOTAC, EASTOTAC, REGALREZ, REGALITE (Eastman), ARKON (Arakawa), NORSOLENE, WINTACK (Cray Valley), NEVTACK LX (Neville Chemical Co.), HIKOTACK, HIKOREZ (Kolon Chemical), NOVARES (Rutgers N.V.), QUINTONE (Zeon), ESCOREZ (Exxonmobile Chemical), NURES, and H-REZ (Newport Industries).

In certain embodiments, the tackifier can include either an elastomeric tackifier, such as polyisobutylene, or a non-elastomeric tackifier, including synthetic polyterpene tackifiers, such as WINGTACK brand tackifiers (e.g., WING- TACK 10, WINGTACK 86, WINGTACK 95, WINGTACK Plus, and WINGTACK Extra) available from Goodyear Chemical Co., Akron, Ohio, or a combination of elastomeric and non-elastomeric tackifiers.

In certain embodiments, the tackifier includes low molecular weight polyisobutylene (viscosity average molecular weight of from 20,000 to 70,000, preferably from 40,000 to 65,000). Suitable low molecular weight polyisobutylene tackifiers are available from Exxon Chemical Company under the trade names VISTANEX LM and VISTANEX L-100, respectively, and include VISTANEX LM-MS (viscosity average molecular weight of 44,000), VISTANEX LM-MH (viscosity average molecular weight of 53,000), and VISTANEX LM-H (viscosity average molecular weight of 63,000).

If used, one or more tackifiers is preferably used in an amount of at least 20 weight percent, and more preferably at least 30 weight percent, based on the total weight of the hydrocolloid composition of the present disclosure. If used, one or more tackifiers is preferably used in an amount of up to 60 weight percent, and more preferably up to 50 weight percent, based on the total weight of the hydrocolloid composition of the present disclosure.

A hydrocolloid composition of the present disclosure may also optionally contain a plasticizer. Plasticizers may be used to provide wetting action and/or viscosity control. These plasticizers are well known in the art and may include hydrocarbon oils, liquid or soft tackifiers, including liquid hydrocarbon resins, liquid polyterpenes, liquid poly(isobutylenes) such as GLISSOPAL, and the like, waxes, and mixtures of oils. A typical plasticizer is mineral oil (Spectrum Corp., Gardena, Calif.).

If used, one or more plasticizers are preferably used in an amount of at least 0.5 weight percent, based on the total weight of the hydrocolloid composition of the present disclosure. If used, one or more plasticizers is preferably used in an amount of up to 10 weight percent, based on the total weight of the hydrocolloid composition of the present disclosure.

Compositions of the present disclosure may also contain minor amounts of other ingredients such as antioxidants, deodorants, perfumes, antimicrobials, and other pharmacologically active agents as is well known in the art.

Compositions of the disclosure can be made by compounding the hydrophobic, unsaturated, elastomeric polymer, the hydrophilic polymer having an unsaturated polymer backbone and polyalkylene ether groups bonded thereto, and optional tackifier and/or plasticizer with a heavy duty mixer until a homogeneous blend is obtained. Alternatively, compositions of the disclosure can be made by compounding the hydrophobic, unsaturated, elastomeric polymer, the reactants that form the hydrophilic polymer having an unsaturated polymer backbone and polyalkylene ether groups bonded thereto, and optional tackifier and/or plasticizer, with a heavy duty mixer until a homogeneous blend is obtained.

Small portions of a dry-blended premix of one or more hydrocolloid absorbents are then typically added and milling continued until a homogeneous dispersion of the absorbents in the polymer phase is obtained. The blended mass can then be molded into sheets for further conversion into wound dressings or formed into shapes such as strips, rings, etc., by any number of means commonly used for converting plastics and elastomers into shapes, such as compression or injection molding. In addition, the blended mass can also be fed into a heated single- or dual-screw extruder and coated from a standard extrusion die to form hydrocolloid compositions in sheets capable of being converted into appropriately shaped materials.

The hydrophobic and hydrophilic polymers are crosslinked to provide a hydrocolloid composition, preferably, an adhesive composition, with a crosslinked matrix including partial unsaturation. Generally, after formation, the hydrocolloid composition, preferably, an adhesive composition, of the present disclosure is irradiated with a dose of ionizing radiation. The crosslinking is typically done at a dose of at least 5 kGy (0.5 Mrad), and preferably at a dose of at least 25 kGy (2.5 Mrad). The crosslinking is typically done at a dose of up to 200 kGy (20 Mrad), and preferably at a dose of up to 50 kGy (5 Mrad).

Both E-beam and gamma irradiation can serve as the ionizing radiation source used to irradiate the hydrocolloid compositions of the present disclosure, and thereby chemically crosslink the hydrophobic, unsaturated, elastomeric polymer and the unsaturated backbone of the hydrophilic polymer components of the adhesive composition. It is likely this crosslinking of the hydrophobic, unsaturated polymer and unsaturated backbone of the hydrophilic polymer components that results in the consistently high wet integrity displayed by the adhesive compositions of the present disclosure. In addition, the application of ionizing radiation can also be used to sterilize the hydrocolloid compositions and/or wound dressings of the present disclosure.

Thus, at least two general methods of forming a hydrocolloid composition are provided by the present disclosure. In one general method, the method includes: compounding a mixture that includes: a hydrophobic, unsaturated, elastomeric polymer (preferably, a homopolymer); a hydrocolloid absorbent (e.g., one selected from the group of a natural hydrocolloid, a semi-synthetic hydrocolloid, a synthetic hydrocolloid, and combinations thereof); a hydrophilic polymer including an unsaturated polymer backbone having polyalkylene ether groups bonded thereto, and optionally a tackifier; and irradiating the mixture with radiation sufficient to crosslink the hydrophobic and hydrophilic polymers and form a composition with a crosslinked matrix having partial unsaturation. In another general method, the method includes: compounding a mixture that includes: a first hydrophobic, unsaturated, elastomeric polymer; a hydrocolloid absorbent; a second hydrophobic, unsaturated polymer (which may or may not be elastomeric); and a hydrophilic polyalkylene oxide-containing compound; and irradiating the mixture with radiation sufficient to crosslink the hydrophobic and hydrophilic polymers and form a composition with a crosslinked matrix that includes partial unsaturation. For example, if desired, some of the hydrophilic polymers can be synthesized in situ. For example, hydrophilic polymers that are made via SN2-type reactions can be readily made in situ (e.g., JEFFAMINE-grafted epoxidized polybutadiene). In this method, a mixture that includes a first hydrophobic, unsaturated, elastomeric polymer, a hydrocolloid absorbent, a second hydrophobic, unsaturated polymer, and a hydrophilic polyalkylene oxide-containing compound can be compounded; and then the mixture irradiated with radiation sufficient to crosslink the hydrophobic and hydrophilic polymers and form a composition with a crosslinked matrix that includes partial unsaturation.

In either general method, the irradiating step can include exposing the mixture to a dose of radiation from 5 kGy to 200 kGy. Such hydrocolloid compositions can then be applied to at least a portion of one major surface of a moisture vapor permeable backing.

Products

Figure 2:
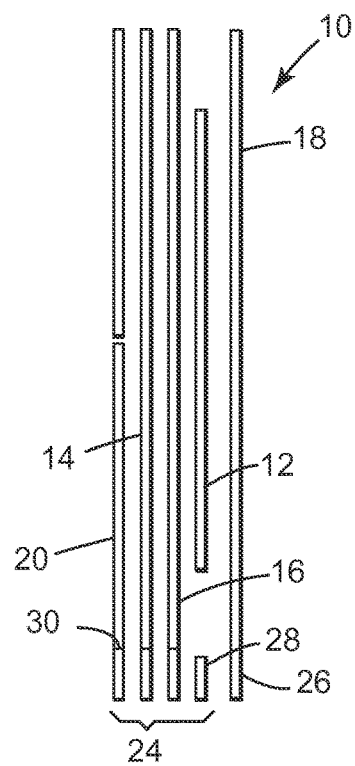
FIG. 2 is an exploded side view of the dressing of FIG. 1.

Referring now to FIGS. 1 and 2, wound dressing 10 includes an oval-shaped sheet 12 of the hydrocolloid composition of the present disclosure. Laminated to the top side (side facing away from the skin when the dressing is in use) is a slightly larger oval-shaped transparent film backing 14. An intermediate layer 16 of a conventional pressure sensitive skin adhesive is used to facilitate lamination. The peripheral portion of the film backing 14 and adhesive layer 16 extends beyond the hydrocolloid sheet 12 to assist in adhering the hydrocolloid sheet 12 to the skin. A conventional release liner 18 is used to protect the exposed surface of the hydrocolloid sheet 12 and the exposed portion of the adhesive layer 16 prior to use. Delivery sheet 20 is attached to the top side of film backing 14 to prevent wrinkling and curling of the edges of backing 14 and adhesive layer 16 after removal of release liner 18. Delivery sheet 20 is divided into two sections of approximately equal size and heat-sealed to the top side of film backing 14. Both sections have a non-heat-sealed edge 22 at the center of the dressing to form handles which facilitate grasping and removal of the delivery sheet. Delivery sheet 20 supports the exposed periphery of backing 14 and adhesive layer 16 during application of the dressing to the patient. Once the dressing is in place on the skin, delivery sheet 20 is removed.

Separation of the release liner 18 from the hydrocolloid sheet 12 and adhesive layer 16 of the dressing 10 is facilitated by two tabs 24 and 26. Tab 24 includes aligned rectangularly-shaped extensions of each of the delivery sheet 20, film backing 14 and adhesive layer 16, and further includes a stiffening member 28 adhered to the adhesive layer 16 to facilitate separation of the tab members from each other. The second tab 26 is aligned with tab 24 and includes a rectangularly-shaped extension of release liner 18. A perforation line 30 separates tab 24 from the main oval section of the dressing. Tab 24 provides an area for the person applying the dressing to hold onto without touching or otherwise contaminating the adhesive 14 and hydrocolloid sheet 12 in the main oval portion of the dressing. After the dressing is in place on the patient, tab 24 can be separated from the main oval portion of the dressing along perforation line 30. In a particularly preferred embodiment, the dressing 10 includes a second opposing tab (not shown) on the opposite side of the dressing 10 from tab 24 to further facilitate the holding and application of the dressing 10 without contamination of the hydrocolloid sheet 12 or wound site.

The film backing 14 is preferably a highly moisture vapor permeable film of, for example, porous polyethylene such as that disclosed in U.S. Pat. No. 4,539,256 or polyurethane such as that described in U.S. Pat. No. 4,598,004. Moisture vapor permeable films of this type allow the wound exudate to evaporate through the dressing and reduce the pooling of exudate under the dressing. The moisture vapor transmission rate of the backing is preferably at least 500 grams/square meter/24 hours when measured at 40° C. and 80 percent humidity differential. Film backing 14 is preferably about 0.026 mm (1 mil) thick.

In a preferred aspect, the film backing 14 further includes a release surface (not shown), such as a low adhesion backsize, coated on the surface of the backing 14 opposite from the hydrocolloid sheet 12 and adhesive layer 16. A commercially available example of a suitable backing with a low adhesion backsize coating for use with the present disclosure is TEGADERM No. 1620 dressing (3M Company, St. Paul, Minn.). By using a film backing 14 containing a release surface, the wound dressing 10 can have other tapes applied over the dressing after its application to a patient. This ability to tape-over the wound dressing allows the dressing to serve as an attachment site or platform for other medical devices. After a period of time, these tapes can be easily removed without disturbing or otherwise having to also remove the wound dressing 10, and thereby expose the wound to further contamination.

Adhesive layer 16 is also preferably moisture vapor permeable so as not to detract significantly from the moisture vapor permeability of the film backing 14. Suitable medical adhesives of this type, such as the copolymer acrylate adhesive and polyvinyl ether adhesive, are described in U.S. Pat. Nos. 4,598,004 and 3,645,535, respectively. The adhesive is preferably about 0.026-0.075 mm (1-3 mils) thick.

Delivery sheet 22 can be a polyester-film with a polyethylene-ethylvinyl acetate heat seal coating.

Hydrocolloid sheet 12 preferably has the compositions as described in the examples below and has a thickness between 1.0-1.75 mm (40-70 mils).

Figure 3:
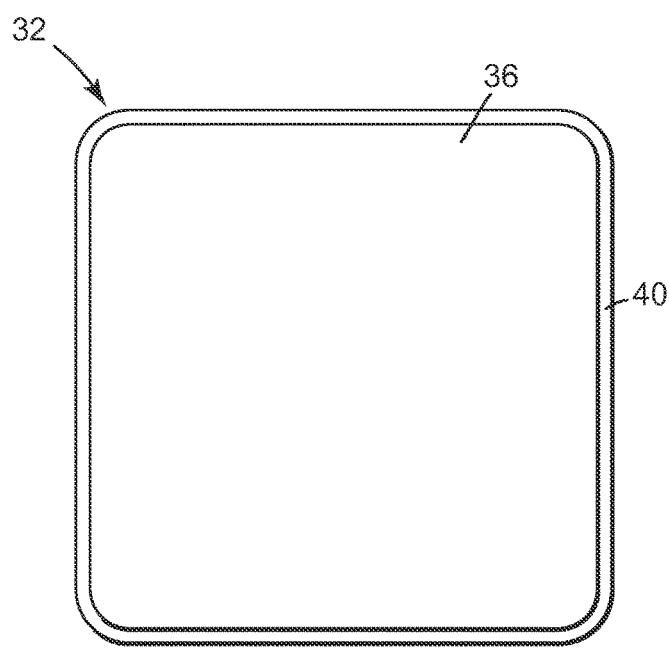
FIG. 3 is a top view of an alternative embodiment of a wound dressing incorporating the hydrocolloid composition of the present disclosure.
Figure 4:
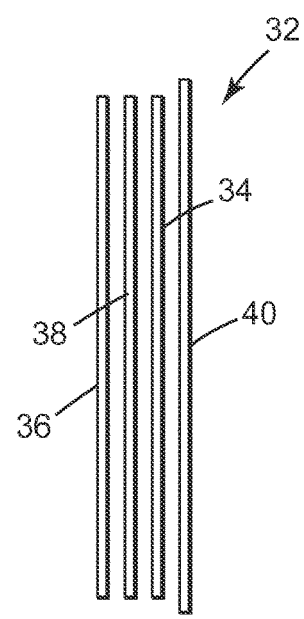
FIG. 4 is an exploded side view of the dressing of FIG. 3.

The dressing of FIGS. 3 and 4 represents an alternative embodiment of a wound dressing 32 which incorporates the hydrocolloid composition of the present disclosure. Dressing 32 includes a square sheet 34 of the hydrocolloid composition. A square film backing 36 of the same dimensions as the hydrocolloid sheet is laminated to the top surface (facing away from the skin) of the hydrocolloid sheet by adhesive layer 38. Release liner 40 covers the exposed surface of hydrocolloid sheet 34 and extends outwardly from the hydrocolloid sheet on all sides to facilitate grasping of the liner 40 and removal thereof prior to application of the dressing to the wound. The materials which can be used to form film backing 34 and adhesive layer 38 are essentially the same as those discussed above in connection with the embodiment of FIGS. 1 and 2. The dressing of FIG. 3 is cheaper to manufacture than the dressing of FIG. 1 and is also easier to cut to the dimensions of the wound.

The hydrocolloid adhesive compositions and dressings of the present disclosure exhibit increased WVTR over other commercially available compositions. Typically, the hydrophilic polymer is present in an amount that increases the WVTR of the hydrocolloid composition (preferably, by at least 50%, or at least 100% (2×), or at least 200%) relative to the same hydrocolloid composition without the hydrophilic polymer. Such WVTR is a measure of the passage of water vapor through a substance as described in the WVTR Test (see Examples Section).

In addition, the compositions and dressings of the disclosure also exhibit adjustable absorbency, high shear holding power, good adhesion to skin, good cohesive strength, good edge adhesion, reduced adhesive cold-flow, and reduced adhesive residues. These performance factors depend on the exact composition of the materials used.

Illustrative Embodiments

1. A hydrocolloid composition comprising:
   a hydrophobic, unsaturated, elastomeric polymer;
   a hydrocolloid absorbent; and
   a hydrophilic polymer comprising an unsaturated polymer backbone having polyalkylene ether groups bonded thereto.
2. The hydrocolloid composition of embodiment 1 wherein the hydrophobic and hydrophilic polymers are crosslinked to provide the composition with a crosslinked matrix comprising partial unsaturation.
3. The hydrocolloid composition of embodiment 1 or 2 which is in the form of an adhesive.
4. The hydrocolloid composition of embodiment 3 which is in the form of a pressure sensitive adhesive.
5. The hydrocolloid composition of any of embodiments 1 through 4 further comprising a tackifier.
6. The hydrocolloid composition of any of embodiments 1 through 5 wherein the hydrophobic, unsaturated, elastomeric polymer is present in an amount of 20-50 wt-%, based on the total weight of the composition.
7. The hydrocolloid composition of any of embodiments 1 through 6 wherein the hydrophilic polymer is present in an amount of 0.5-20 wt-%, based on the total weight of the composition.
8. The hydrocolloid composition of any of embodiments 1 through 7 wherein the hydrocolloid absorbent is present in an amount of 5-60 wt-%, based on the total weight of the composition.
9. The hydrocolloid composition of any of embodiments 1 through 8 wherein the polyalkylene ether groups are derived from a hydrophilic polyalkylene oxide-containing compound.
10. The hydrocolloid composition of embodiment 9 wherein the hydrophilic polyalkylene oxide-containing compound comprises ethylene oxide units and optionally co-polymerized propylene oxide units.
11. The hydrocolloid composition of embodiment 10 wherein the hydrophilic polyalkylene oxide-containing compound comprises at least 70 wt-% ethylene oxide units, based on the total weight of the polyalkylene oxide-containing compound.
12. The hydrocolloid composition of any of embodiments 1 through 8 wherein the polyalkylene ether groups comprise at least 70 wt-% ethylene oxide units, based on the total weight of a polyalkylene oxide-containing compound used to prepare the hydrophilic polymer.
13. The hydrocolloid composition of any of embodiments 1 through 12 wherein the hydrophilic polymer comprises 20-95 wt-% hydrophobic polymer backbone and 5-80 wt-% hydrophilic polyalkylene ether groups bonded thereto, based on the total weight of the hydrophilic polymer.
14. The hydrocolloid composition of any of embodiments 1 through 13 wherein the hydrophilic polymer is derived from an optionally functionalized hydrophobic, unsaturated polymer (which may or may not be elastomeric) and a hydrophilic polyalkylene oxide-containing compound.
15. The hydrocolloid composition of embodiment 14 wherein the optionally functionalized unsaturated polymer is selected from optionally functionalized polybutadiene, polyisoprene, a butyl rubber which is optionally halogenated, and combinations thereof.
16. The hydrocolloid composition of embodiment 14 or 15 wherein the optionally functionalized hydrophobic, unsaturated polymer and the hydrophilic polyalkylene oxide-containing compound are reacted in a weight ratio from 7:3 to 3:7.
17. The hydrocolloid composition of any of embodiments 1 through 16 wherein the hydrophobic, unsaturated, elastomeric polymer is selected from polybutadiene, polyisoprene, a butyl rubber which is optionally halogenated, and combinations thereof.
18. The hydrocolloid composition of any of embodiments 1 through 17 comprising:
   a hydrophobic, unsaturated, elastomeric homopolymer;
   a tackifier;
   a hydrocolloid absorbent selected from the group of a natural hydrocolloid, a semi-synthetic hydrocolloid, a synthetic hydrocolloid, and combinations thereof; and
   a hydrophilic polymer comprising an unsaturated polymer backbone having polyalkylene ether groups bonded thereto;
   wherein the hydrophobic and hydrophilic polymers are crosslinked by 5-200 kGy gamma radiation to provide an adhesive composition with a crosslinked matrix.
19. The hydrocolloid composition of any of embodiments 1 through 18 wherein the hydrocolloid absorbent is selected from the group of pectin, gelatin, a carboxymethylcellulose, a crosslinked carboxymethylcellulose, a crosslinked polyacrylic acid, and combinations thereof.
20. The hydrocolloid composition of any of embodiments 1 through 19 further comprising a plasticizer.
21. The hydrocolloid composition of any of embodiments 1 through 20 wherein the hydrophilic polymer is present in an amount that increases the WVTR of the hydrocolloid composition relative to the same hydrocolloid composition without the hydrophilic polymer.
22. The hydrocolloid composition of embodiment 21 wherein the hydrophilic polymer is present in an amount that increases the WVTR of the hydrocolloid composition by at least 50% relative to the same hydrocolloid composition without the hydrophilic polymer.
23. A hydrocolloid composition comprising:
   20-50 wt-% of a hydrophobic, unsaturated, elastomeric homopolymer;
   5-60 wt-% of a hydrocolloid absorbent; and
   0.5-20 wt-% of a hydrophilic polymer comprising an unsaturated polymer backbone having polyalkylene ether groups bonded thereto;
   wherein the hydrocolloid composition is in the form of a pressure sensitive adhesive; and
   wherein the hydrophilic polymer is present in an amount that increases the WVTR of the hydrocolloid composition relative to the same hydrocolloid composition without the hydrophilic polymer.
24. A wound dressing comprising the hydrocolloid composition of any of embodiments 1 through 23 coated on a surface of a moisture vapor permeable backing.
25. The wound dressing of embodiment 24 wherein the backing further comprises a release coating coated on the surface of the backing opposite the surface coated with the hydrocolloid composition.
26. The wound dressing of embodiment 24 or 25 wherein the backing is a transparent film of polyurethane or porous polyethylene.
27. The wound dressing of any of embodiments 24 through 26 wherein the backing extends beyond the periphery of the hydrocolloid composition coating on all sides, and wherein at least a portion of the extended backing surface is coated with a second pressure sensitive adhesive.

28. A method of treating a wound comprising applying to the wound the hydrocolloid composition of any of embodiments 1 through 23 or the wound dressing of any of embodiments 24 through 27.
29. An ostomy pouch comprising a hydrocolloid composition of any of embodiments 1 through 23.
30. A method of forming a hydrocolloid composition, the method comprising:
compounding a mixture comprising:
a hydrophobic, unsaturated, elastomeric polymer;
a hydrocolloid absorbent; and
a hydrophilic polymer comprising an unsaturated polymer backbone having polyalkylene ether groups bonded thereto; and
irradiating the mixture with radiation sufficient to crosslink the hydrophobic and hydrophilic polymers and form a composition with a crosslinked matrix comprising partial unsaturation.
31. The method of embodiment 30 wherein irradiating the mixture comprises exposing the mixture to a dose of radiation from 5 kGy to 200 kGy.
32. The method of embodiment 30 or 31 wherein the mixture comprises:
a hydrophobic, unsaturated, elastomeric homopolymer;
a tackifier;
a hydrocolloid absorbent selected from the group of a natural hydrocolloid, a semi-synthetic hydrocolloid, a synthetic hydrocolloid, and combinations thereof; and
a hydrophilic polymer comprising an unsaturated polymer backbone having polyalkylene ether groups bonded thereto.
33. The method of any of embodiments 30 through 32 further comprising preparing the hydrophilic polymer by a method comprising grafting hydrophilic polyalkylene oxide groups to an optionally functionalized hydrophobic, unsaturated polymer.
34. The method of any of embodiments 30 through 33 further comprising applying the hydrocolloid composition to at least a portion of one major surface of a moisture vapor permeable backing.
35. A method of forming a hydrocolloid composition, the method comprising:
compounding a mixture comprising:
a first hydrophobic, unsaturated, elastomeric polymer;
a hydrocolloid absorbent;
a second hydrophobic, unsaturated polymer; and
a hydrophilic polyalkylene oxide-containing compound; and
irradiating the mixture with radiation sufficient to crosslink the hydrophobic and hydrophilic polymers and form a composition with a crosslinked matrix that includes partial unsaturation.
36. A hydrophilic polymer comprising an unsaturated polymer backbone having pendant polyalkylene ether groups bonded thereto.
37. The hydrophilic polymer of embodiment 36 having the following structure:

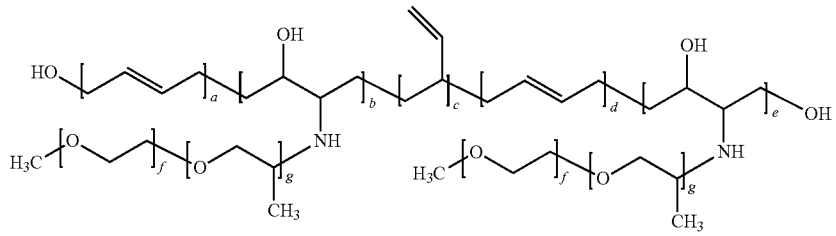

wherein a+b+c+d+e=10-2000 and g+f=5-250.
38. The hydrophilic polymer of embodiment 37 wherein a+b+c+d+e=10-2000, g=3, and f=19.
39. The hydrophilic polymer of embodiment 36 having the following structure:

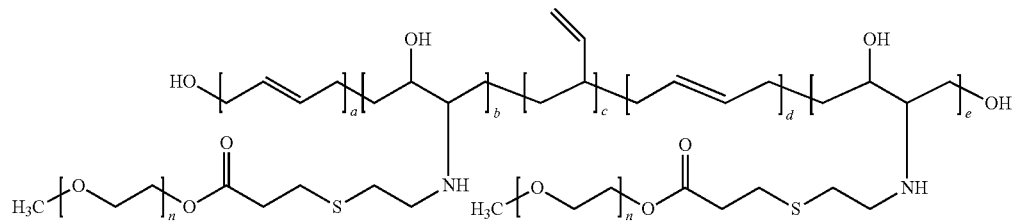

wherein a+b+c+d+e=10-2000, and each n is independently 5-50.

40. The hydrophilic polymer of embodiment 36 having the following structure:

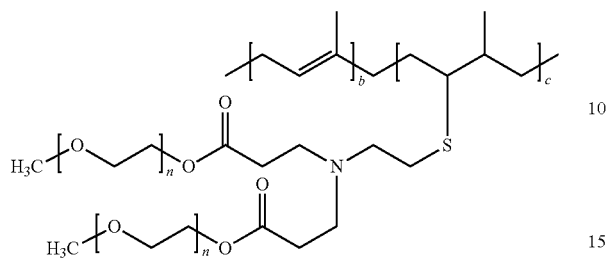

wherein b+c=10-2000, and each n is independently 5-50.

41. The hydrophilic polymer of embodiment 36 having the following structure:

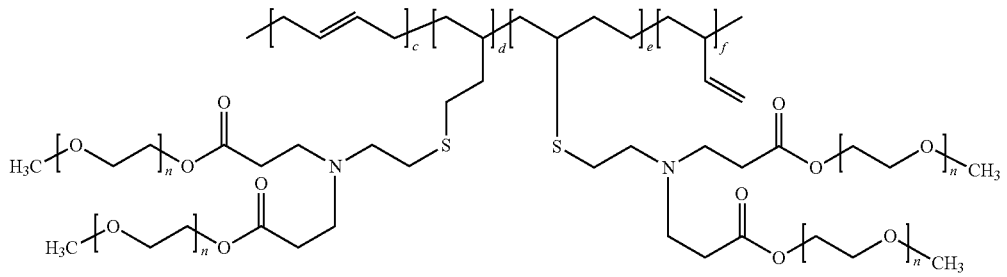

wherein c+d+e+f=10-2000, and each n is independently 5-50.

42. The hydrophilic polymer of embodiment 36 having the following structure:

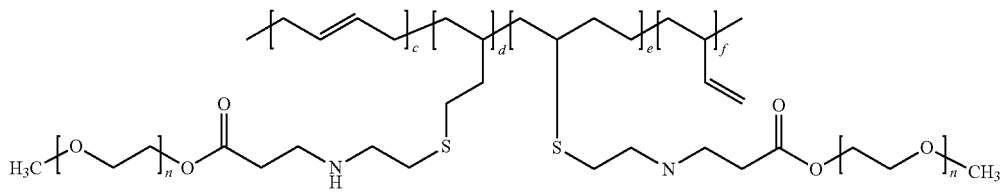

wherein c+d+e+f=10-2000, and each n is independently 5-50.

EXAMPLES

TABLE 1

Materials used in Examples

| Name/Trade name | Manufacturer | Material | Comments |
|---|---|---|---|
| JEFFAMINE M1000 | Huntsman (Woodlands, TX) | Polyethermonoamine | ~1000 molecular weight PO/EO ratio of 3/19 |
| Poly BD 605E | Cray Valley (Exton, PA) | Hydroxyl terminated epoxidized polybutadiene | Low molecular weight liquid rubber. |
| RICON 130 | Cray Valley (Exton, PA) | Polybutadiene | Low molecular weight liquid rubber. |
| LIR30 | Kuraray (Pasadena, TX) | Polyisoprene | Low molecular weight liquid rubber. |

TABLE 1-continued

Materials used in Examples

| Name/Trade name | Manufacturer | Material | Comments |
|---|---|---|---|
| IRGACURE 651 | BASF (Florham Park, NJ) | 2,2-Dimethoxy-1,2-diphenylethan-1-one | UV radical generator |
| 2-aminoethanethiol | TCI America (Portland, OR) | | |
| NATSYN 2210 | Goodyear (Akron, OH) | Polyisoprene | |
| Oppanol B12 SFN | BASF (Florham Park, NJ) | Polyisobutylene | |
| CMC-PE32 FG-X | S & G Resources, Inc., (Medfield, MA) | Carboxymethyl cellulose | |
| Ac-Di-Sol SD-711 | FMC Biopolymer, (Philadelphia, PA) | Crosslinked polycarboxymethyl cellulose | |
| Ethylene Oxide monomer (EOA) | 3M | Acrylate monomer from Carbowax 750 (Dow) and acrylic acid | See U.S. Pat. No. 5,648,166, Example 3 for synthesis. |

Equipment

Hot-Melt Mixer (C.W. Brabender Instruments, Inc. South Hackensack, N.J. Type Six Mixer).

Temperature controllable hot press (Carver Inc, Wabash, Ind. Model 2699).

Environmental temperature and humidity test chamber (Thermotron, Holland, Mich. Model SM-8S-L/H).

Vacuum oven (VWR, Economy Series, Catalogue number 52201-218).

Hydrophilic Additive Preparation

Examples 1 to 7 describe the synthesis of hydrophilic additives No. 1 to No. 7 respectively.

Example 1

Hydrophilic Additive No. 1

In a three-neck, 500 mL round-bottomed flask equipped with a thermometer, a mechanical stirrer, and a nitrogen inlet was placed liquid epoxidized polybutadiene (Cray Valley, Poly BD 605E) (100 g) and monoamine terminated polyether (Huntsman, JEFFAMINE M1000) (100 g). The contents were stirred with a mechanical stirrer under nitrogen atmosphere at 60° C. until the mixture became homogeneous liquid. Once a clear liquid was obtained, the solution temperature was increased to 80° C. After 1 hour of mixing at 80° C., the solution was poured into a 250-mL glass jar and the reaction was cooled to room temperature. At room temperature, the product was a slightly yellow soft solid. The structure of Hydrophilic Additive No. 1 is:

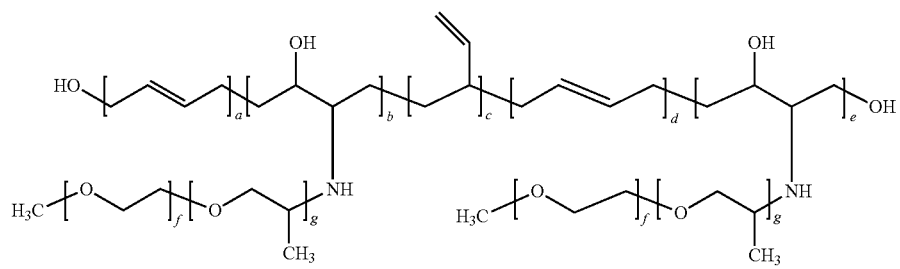

wherein $a+b+c+d+e=20-30$, $g=3$, and $f=19$. The ratio of backbone PolyBD 605E to pendant groups (JEFFAMINE M1000) is 50:50.

Example 2

Hydrophilic Additive No. 2

Hydrophilic additive 2 was synthesized by following the process in Example 1 with different amounts of PolyBD 605E and JEFFAMINE M1000. Thirty grams (30 g) of Poly BD 605E was reacted with 70 g of JEFFAMINE M1000. The structure of Hydrophilic Additive No. 2 is:

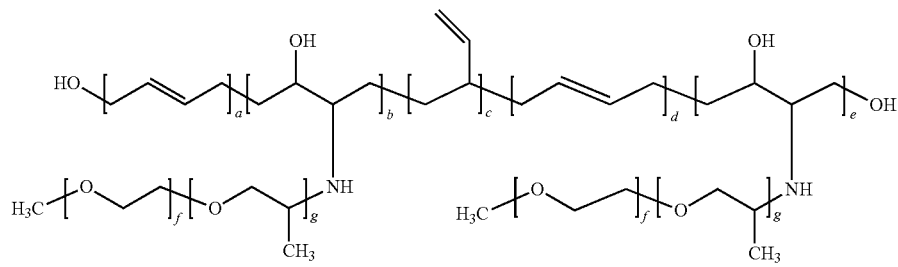

wherein a+b+c+d+e=20-30, g=3, and f=19. The ratio of backbone Poly BD 605E to pendant groups (JEFFAMINE M1000) is 30:70.

Example 3

Hydrophilic Additive No. 3

Hydrophilic additive 3 was synthesized by following the process in Example 1 with different amounts of PolyBD 605E and JEFFAMINE M1000. Seventy grams (70 g) of Poly BD 605E was reacted with 30 g of JEFFAMINE M1000. The structure of Hydrophilic Additive No. 3 is:

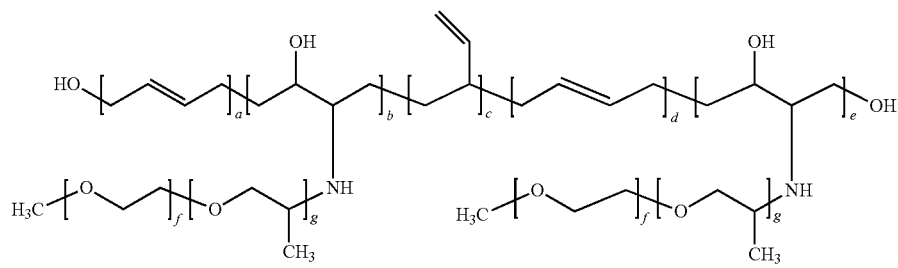

wherein a+b+c+d+e=20-30, g=3, and f=19. The ratio of backbone PolyBD 605E to pendant groups (JEFFAMINE M1000) is 70:30.

Example 4

Hydrophilic Additive No. 4

In a three-neck, round-bottomed 250 mL flask equipped with a thermometer, and a nitrogen inlet was placed ethylene oxide monomer (EOA, made by the method described in Example 3 of U.S. Pat. No. 5,648,166) (50.0 g), 2-aminoethanethiol (4.79 g), IRGACURE 651 (0.25 g), and toluene (30.0 g). The contents of the flask were stirred with a magnetic stir bar under nitrogen at 25° C. until all components dissolved to form a homogeneous solution. Once a clear solution was formed, the solution was irradiated with a low intensity ultraviolet light (Silvania Blacklight Blue F15T8/BLB, 15 W) for 25 minutes (min). The resulting solution was dried with a rotary evaporator to remove toluene. The structure of the resultant ethylene oxide acrylate is:

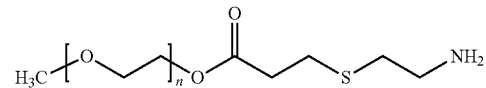

wherein n is 15 to 20.

Fifteen (15) grams of the dried material was charged in a 100 mL round bottom flask equipped with a thermometer, a mechanical stirrer, and a nitrogen inlet with liquid epoxidized polybutadiene (Cray Valley, Poly BD 605E) (30 g). The contents were stirred with a mechanical stirrer under nitrogen atmosphere at 60° C. until the mixture became homogeneous liquid. Once a clear liquid was obtained, the solution temperature was increased to 80° C. After 1 hour of mixing at 80° C., the solution was poured into a 100-mL glass jar and the reaction was cooled to room temperature. At room temperature, the product was a slightly yellow soft solid. The structure of Hydrophilic Additive No. 4 is:

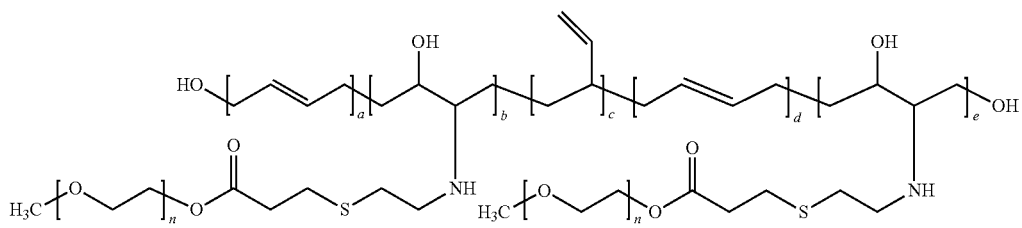

wherein a+b+c+d+e=20-30, and each n is independently 15-20.

Example 5

Hydrophilic Additive No. 5

In a three-neck, round-bottomed 250-mL flask equipped with a thermometer, and a nitrogen inlet was placed ethylene oxide monomer (EOA) (75.0 g) and 2-aminoethanethiol (7.19 g). The contents of the flask were stirred with a mechanical stirrer under nitrogen at 60° C. until all components became a homogeneous mixture. Once a clear blend was formed, the solution temperature was increased to 90° C. After 2 hours of mixing at 90° C., the solution was poured into a 100-mL glass jar and the reaction was cooled to room temperature. At room temperature, the product was a slightly yellow soft solid. The structure of the resultant ethylene oxide acrylate is:

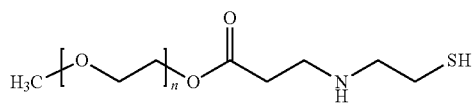

wherein n is 15 to 20.

Fifteen (15) grams of the resulting material was charged in a three-neck, round-bottomed 100 mL flask equipped with a thermometer, and a nitrogen inlet with liquid polybutadiene (RICON 130) (30.0 g) and IRGACURE 651 0.1 g. The contents of the flask were stirred under nitrogen at 60° C. until a homogeneous solution was formed. Once a transparent solution was formed, the mixture was irradiated with a low intensity ultraviolet light (Silvania Blacklight Blue F15T8/BLB, 15 W) for 25 min. After the irradiation, the product was cooled to room temperature. The structure of Hydrophilic Additive No. 5 is:

Example 6

Hydrophilic Additive No. 6

In a three-neck, round-bottomed 250-mL flask equipped with a thermometer, and a nitrogen inlet was placed ethylene oxide monomer (EOA) (70.0 g) and 2-aminoethanethiol (3.33 g). The contents of the flask were stirred with a mechanical stirrer under nitrogen at 60° C. until all components melt to form a homogeneous mixture. Once a clear blend was formed, the reaction temperature was increased to 90° C. After 2 hours of mixing at 90° C., the solution was poured into a 100 ml glass jar and the reaction was cooled to room temperature. At room temperature, the product was a slightly yellow soft solid. The structure of the resultant ethylene oxide acrylate is:

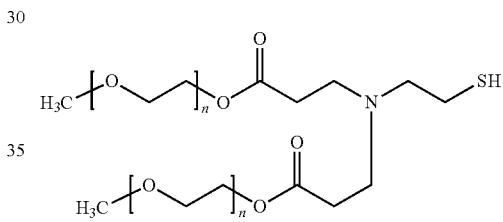

wherein n is 15 to 20.

Ten (10) grams of the resulting material was charged in a three-neck, round-bottomed 100 mL flask equipped with a thermometer, and a nitrogen inlet with liquid polyisoprene (LIR30) (15.0 g), toluene (35 g) and IRGACURE 651 0.1 g. The contents of the flask were stirred under nitrogen at room temperature until a homogeneous solution was formed. Once a transparent solution was formed, the mixture was irradiated with a low intensity ultraviolet light (Silvania Blacklight Blue F15T8/BLB, 15 W) for 25 min. After the irradiation, the product was dried with a rotary evaporator by removing toluene. The structure of Hydrophilic Additive No. 6 is:

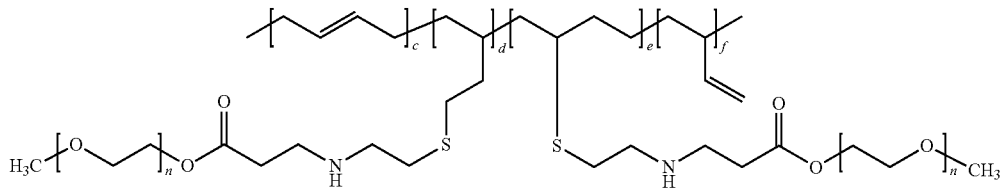

wherein c+d+e+f=40-50, and each n is independently 15-20.

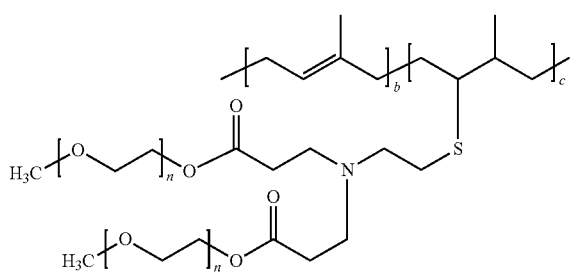

wherein c+d+e+f=400-450, and each n is independently 15-20.

Example 7

Hydrophilic Additive No. 7

In a three-neck, round-bottomed 250-mL flask equipped with a thermometer, and a nitrogen inlet was placed ethylene oxide monomer (EOA) (70.0 g) and 2-aminoethanethiol (3.33 g). The contents of the flask were stirred with a mechanical stirrer under nitrogen at 60° C. until all components dissolved to form a homogeneous solution. Once a clear solution was formed, the solution temperature was increased to 90° C. After 2 hours of mixing at 90° C., the solution was poured into a 100-mL glass jar and the reaction was cooled to room temperature. At room temperature, the product was a slightly yellow soft solid. The structure of the resultant ethylene oxide acrylate is:

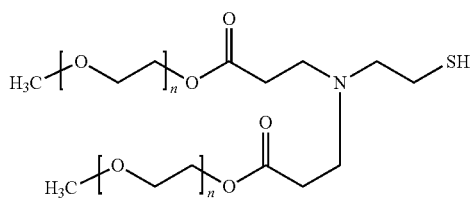

wherein n is 15 to 20.

Ten (10) grams of the resulting material was charged in a three-neck, round-bottomed 100-mL flask equipped with a thermometer, and a nitrogen inlet with liquid polybutadiene (RICON130) (15.0 g), toluene (35 g) and IRGACURE 651 0.1 g. The contents of the flask were stirred under nitrogen at room temperature until a homogeneous solution was formed. Once a transparent solution was formed, the mixture was irradiated with a low intensity ultraviolet light (Silvania Blacklight Blue F15T8/BLB, 15 W) for 25 min. After the irradiation, the product was dried with a rotary evaporator by removing toluene. The structure of Hydrophilic Additive No. 7 is:

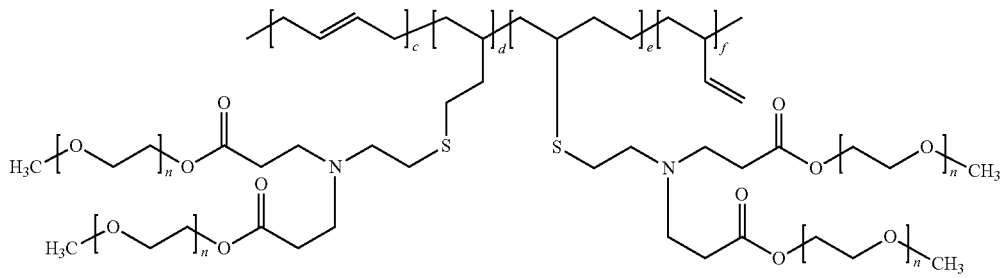

wherein c+d+e+f=40-50, and each n is independently 15-20.

Hydrocolloids Sample Preparation

The hydrocolloid samples were prepared by a two-step procedure. For each sample in Examples 8-12, all ingredients were blended in a heated hot melt mixer with a mixing speed of 100 revolutions per minute (RPM) at 100° C. for 10-20 minutes. Samples were degassed in a vacuum oven at 65° C. under reduced pressure for 2 days prior to hot pressing to reduce entrapped air. Hot pressing of samples were done at 140° C. with 9-mil shims between two release liners and a maximum load of 20,000-24,000 pounds. Pressed samples were then cold laminated to an extruded polyurethane film (Estane, Lubrizol Corporation, 0.8 mils) prior to gamma irradiation (30-40 kGy, to activate the cross-linking of the additive into the adhesive matrix and also to simulate gamma sterilization)

Examples 8-12

Example 8 was made without any additives and served as the control. In Examples 9 to 12, the same additive was used with increasing additive concentration while the concentration of hydrocolloid particles was kept constant.

TABLE 2

| Composition of Examples 8-12 | | | | | |
|---|---|---|---|---|---|
| Example | 8 (control) | 9 | 10 | 11 | 12 |
| Polyisoprene (NATSYN 2210) | 32.5% | 30.0% | 27.5% | 25.0% | 22.5% |
| Polyisobutylene (Oppanol B-12 SFN) | 40.0% | 37.5% | 35.0% | 32.5% | 30.0% |
| Carboxymethyl cellulose (CMC-PE32 FG-X) | 15.0% | 15.0% | 15.0% | 15.0% | 15.0% |
| AC-DI-SOL SD-711 | 12.5% | 12.5% | 12.5% | 12.5% | 12.5% |
| Hydrophilic Additive #1 | 0.0% | 5.0% | 10.0% | 15.0% | 20.0% |

Water Vapor Transmission Rate Measurement

For a hydrocolloid wound dressing, the material is typically directly in contact with wound exudate so the appropriate test for water vapor transmission rate (WVTR) would be the ASTM E-96 (Standard test method for water vapor transmission of materials, Procedure BW), inverted water method. During initial material testing, when a porous backing was used with the inverted water method, it was observed that water would drip through the material at around 18 hours of exposure. This suggested that water could fairly easily migrate through the hydrocolloid so it was decided an occlusive backing should be used and testing based on ASTM E-96, Procedure D (Water method at 90° F.). As hydrocolloids typically have a low WVTR, it was decided to run this test with a variance on temperature (40° C.) and relative humidity (20%) to allow better detection of weight loss over time. The measurement orifice was a ½ inch diameter circular hole. At least 5 replicates were tested at the same time. Samples were equilibrated for 4 hours in the test condition prior to the start of the test. All WVTR data shown use this test condition and reported with the unit of g/m²/24 hours.

TABLE 3

WVTR of Examples 8-12

| Example | 8 (Control) | 9 | 10 | 11 | 12 |
|---|---|---|---|---|---|
| Additive amount (%) | 0 | 5 | 10 | 15 | 20 |
| WVTR (±95% confidence) | 105 ± 44 | 694 ± 145 | 842 ± 41 | 920 ± 39 | 1044 ± 179 |

Figure 5:
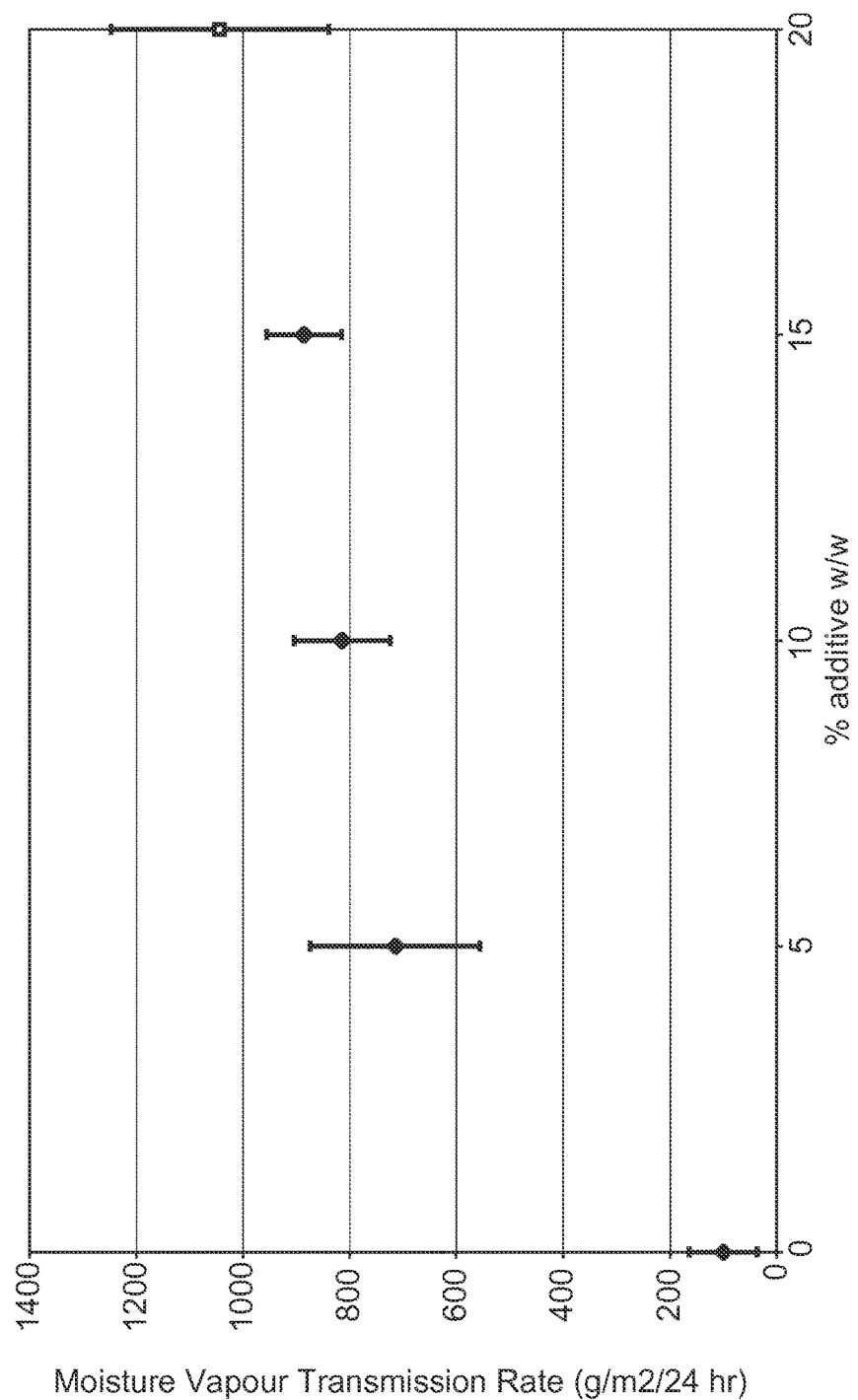
FIG. 5 is a graph showing the change in WVTR with increasing additive concentration.

In Examples 8-12, by increasing the hydrophilic additive amount (which increases the number of hydrophilic groups in the matrix), the WVTR increased approximately 10 times at 20% of the additive (FIG. 5). The increase is most dramatic at 5% of additive, compared with no additive. Between 5% and 20%, the increase is gradual.

Examples 13-18

For hydrophilic additives No. 2 to No. 7, the ratios of hydrophilic groups to the backbone were different to the first additive. In Examples 13 to 18, the percentage of PEG functionality in the matrix was maintained by adjusting the concentration of the additive in the mixture (Table 4). The processing and WVTR testing were the same as shown for Examples 8-12.

TABLE 4

Composition of Examples 13-18

| | Example | | | | | |
|---|---|---|---|---|---|---|
| | 13 | 14 | 15 | 16 | 17 | 18 |
| Polyisoprene (NATSYN 2210) | 30.7% | 28.3% | 28.7% | 28.7% | 29.4% | 29.4% |
| Polyisobutylene (Oppanol B-12 SFN) | 38.2% | 35.8% | 36.3% | 36.3% | 36.9% | 36.9% |
| Carboxymethyl cellulose (CMC-PE32 FG-X) | 15.0% | 15.0% | 15.0% | 15.0% | 15.0% | 15.0% |
| AC-DI-SOL SD-711 | 12.5% | 12.5% | 12.5% | 12.5% | 12.5% | 12.5% |
| Additive amount | 3.6% | 8.3% | 7.5% | 7.5% | 6.2% | 6.2% |
| Hydrophilic Additive used | #2 | #3 | #4 | #5 | #6 | #7 |

TABLE 5

WVTR of Examples 13-18

| | Example | | | | | |
|---|---|---|---|---|---|---|
| | 13 | 14 | 15 | 16 | 17 | 18 |
| Additive amount (%) | 3.6 | 8.3 | 7.5 | 7.5 | 6.2 | 6.2 |
| WVTR (±95% confidence) | 404 ± 36 | 569 ± 36 | 434 ± 29 | 374 ± 60 | 374 ± 0 | 389 ± 29 |

Figure 6:
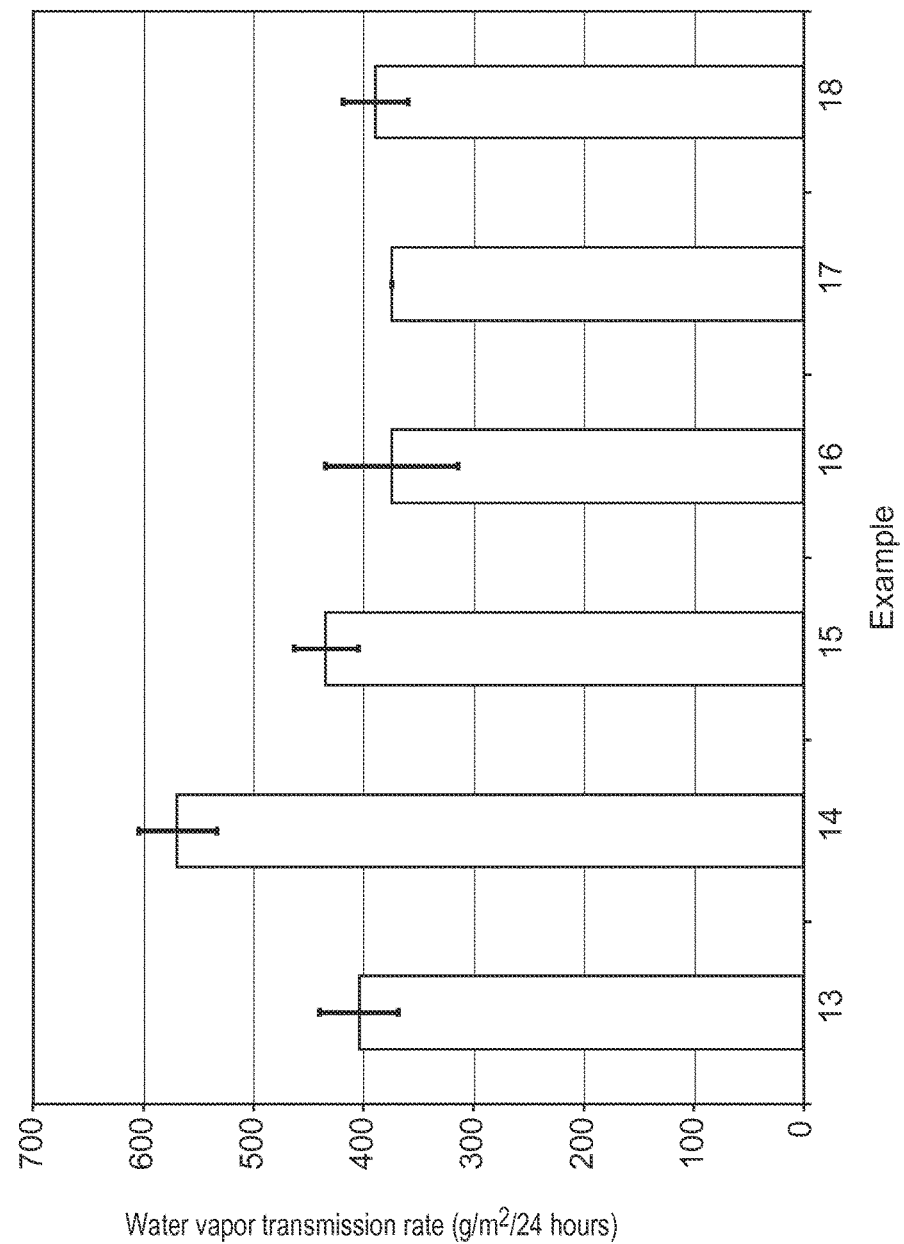
FIG. 6 is a graph showing the WVTR of samples with similar amounts of hydrophilic groups.

With the amount of hydrophilic groups fixed in the final formulation, the WVTR in Examples 13-18 (Table 5 and FIG. 6) show that they are similar to each other, with Example 14 being the exception. The potential reason is that as Example 14 has a higher concentration of additive (FIG. 5), it may be disrupting the hydrophobic matrix more than the other formulations and causing an additive contribution to the change in WVTR.

WVTR of Commercial Products Compared to Examples 9 and 12

Figure 7:
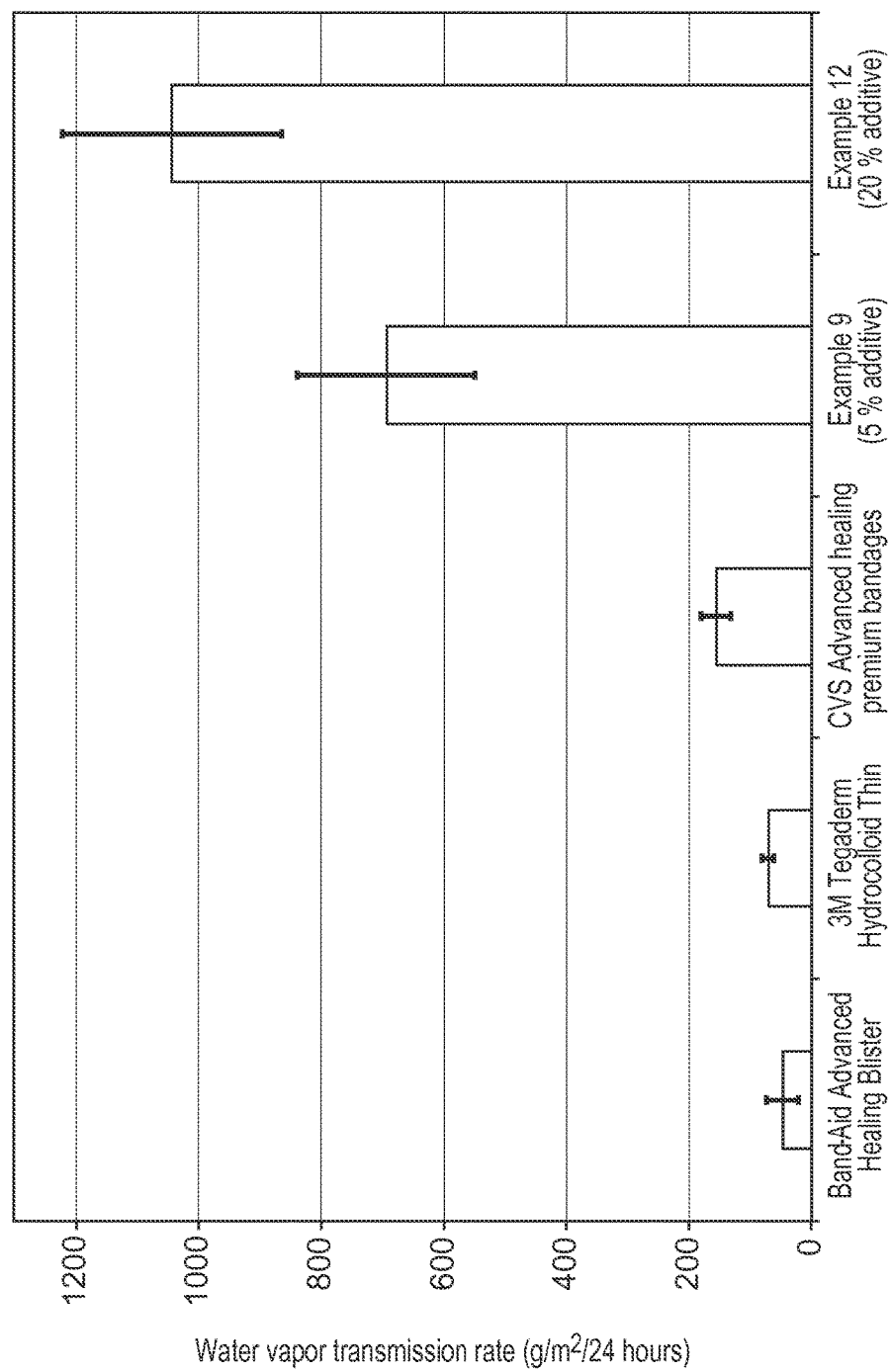
FIG. 7 is a graph showing the WVTR of commercially available hydrocolloid products compared to that of Examples 9 and 12 of the present disclosure.

While the examples prepared above are not in the final product form, it is still possible to compare the WVTR of each to that of commercial hydrocolloids tested under the same conditions. Three commercially available products containing hydrocolloids were tested for WVTR as described above and compared to the WVTR of Examples 9 and 12 (FIG. 7). Although thicknesses are different between the samples, which can influence the WVTR, the compositions of the present disclosure that include a hydrophilic polymer have significantly higher WVTR than the commercially available products.

Figure 8A:
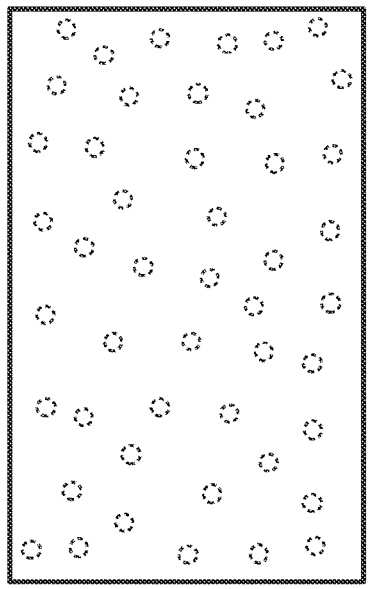
FIG. 8A-8D illustrate a schematic diagram showing a proposed mechanism of the present disclosure.
Figure 8B:
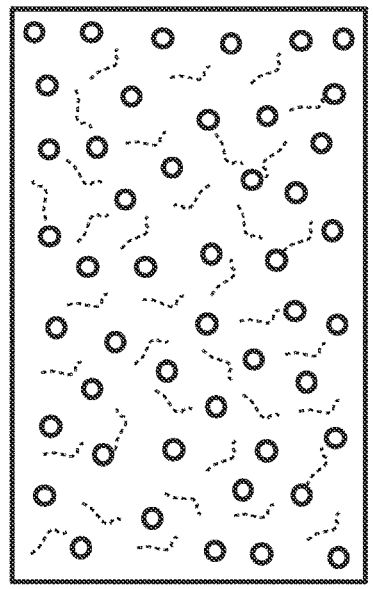
Figure 8C:
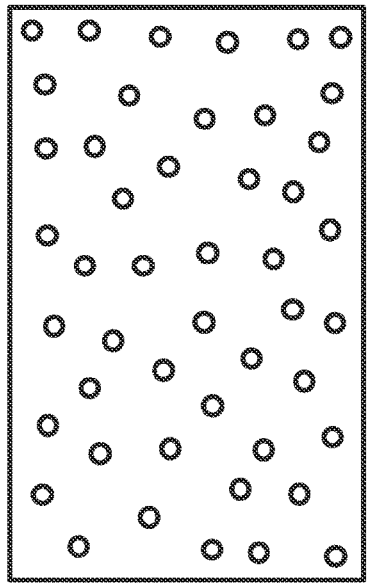

It is believed that when hydrophilic hydrocolloid particles (e.g., Carboxymethyl cellulose, CMC) are mixed into a hydrophobic matrix (e.g., polyisoprene), as in the commercial products listed in FIG. 7, they are typically gathered in discrete zones (as shown in FIG. 8A), depending on how well the composition is mixed. If the hydrophilic hydrocolloid particles are substituted for hydrophilic particles (e.g., Polyethylene glycol, PEG), the same would happen (as shown in FIG. 8B). If CMC and PEG are both mixed into the matrix, they would be likely to be associated with each other in a 'collapsed' state either as pure CMC, pure PEG, or a mixture of each, as the majority of the material in the matrix is hydrophobic (as shown in FIG. 8C).

Figure 8D:
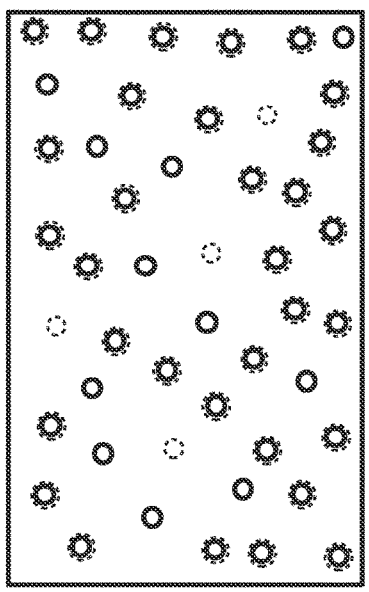

Although not intending to be limited by theory, it is believed that the significantly improved WVTR is due to the fact that as PEG is tethered to a hydrophobic backbone, it is less likely for it to be collapsed completely (FIG. 8D). Such groups would be attracted to other hydrophilic groups dispersed throughout the matrix to associate with. By doing so, it is believed that pathways are created that are more hydrophilic than others. These pathways provide avenues for water vapor to migrate through the matrix.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A hydrocolloid composition comprising:
   a hydrophobic, unsaturated, elastomeric polymer;
   a hydrocolloid absorbent; and a hydrophilic polymer comprising an unsaturated polymer backbone having polyalkylene ether pendant groups bonded thereto,
wherein the polyalkylene ether groups are derived from a hydrophilic polyalkylene oxide-containing compound and wherein the hydrophilic polyalkylene oxide-containing compound comprises ethylene oxide units and optionally co-polymerized propylene oxide units,
wherein the unsaturated polymer backbone comprises one of epoxidized polyubutadiene, polyubutadiene and polyisoprene, and
wherein the hydrophilic polymer is present in an amount that increases the water vapor transmission rate (WVTR) of the hydrocolloid composition relative to the same hydrocolloid composition without the hydrophilic polymer.

2. The hydrocolloid composition of claim 1 wherein the hydrophobic and hydrophilic polymers are crosslinked to provide the composition with a crosslinked matrix comprising partial unsaturation.

3. The hydrocolloid composition of claim 2 which is in the form of an adhesive.

4. The hydrocolloid composition of claim 3 which is in the form of a pressure sensitive adhesive.

5. The hydrocolloid composition of claim 1 wherein the hydrophobic, unsaturated, elastomeric polymer is present in an amount of 20-50 wt-%, based on the total weight of the composition.

6. The hydrocolloid composition of claim 1 wherein the hydrophilic polymer is present in an amount of 0.5-20 wt-%, based on the total weight of the composition.

7. The hydrocolloid composition of claim 1 wherein the hydrocolloid absorbent is present in an amount of 5-60 wt-%, based on the total weight of the composition.

8. The hydrocolloid composition of claim 1 wherein the polyalkylene ether groups comprise at least 70 wt-% ethylene oxide units, based on the total weight of a polyalkylene oxide-containing compound from which the hydrophilic polymer is derived.

9. The hydrocolloid composition of claim 1 wherein the hydrophilic polymer comprises 20-95 wt-% hydrophobic polymer backbone and 5-80 wt-% hydrophilic polyalkylene ether groups bonded thereto, based on the total weight of the hydrophilic polymer.

10. The hydrocolloid composition of claim 1 wherein the hydrophilic polymer is derived from an optionally functionalized hydrophobic, unsaturated, elastomeric polymer and a hydrophilic polyalkylene oxide-containing compound.

11. The hydrocolloid composition of claim 1 comprising:
a hydrophobic, unsaturated, elastomeric homopolymer;
a tackifier;
a hydrocolloid absorbent selected from the group of a natural hydrocolloid, a semi-synthetic hydrocolloid, a synthetic hydrocolloid, and combinations thereof; and
a hydrophilic polymer comprising an unsaturated polymer backbone having polyalkylene ether groups bonded thereto;
wherein the hydrophobic and hydrophilic polymers are crosslinked by 5-200 kGy gamma radiation to provide an adhesive composition with a crosslinked matrix.

12. The hydrocolloid composition of claim 1 wherein the hydrophilic polymer is present in an amount that increases the WVTR of the hydrocolloid composition by at least 50% relative to the same hydrocolloid composition without the hydrophilic polymer.

13. A hydrocolloid composition comprising:
20-50 wt-% of a hydrophobic, unsaturated, elastomeric homopolymer;
5-60 wt-% of a hydrocolloid absorbent; and
0.5-20 wt-% of a hydrophilic polymer comprising an unsaturated polymer backbone having polyalkylene ether pendant groups bonded thereto;
wherein the polyalkylene ether groups are derived from a hydrophilic polyalkylene oxide-containing compound and wherein the hydrophilic polyalkylene oxide-containing compound comprises ethylene oxide units and optionally co-polymerized propylene oxide units,
wherein the unsaturated polymer backbone comprises one of epoxidized polyubutadiene, polyubutadiene and polyisoprene,
wherein the hydrocolloid composition is in the form of a pressure sensitive adhesive; and
wherein the hydrophilic polymer is present in an amount that increases the WVTR of the hydrocolloid composition relative to the same hydrocolloid composition without the hydrophilic polymer.

14. A wound dressing comprising the hydrocolloid composition of claim 1 coated on a surface of a moisture vapor permeable backing.

15. The wound dressing of claim 14 wherein the backing further comprises a release coating coated on the surface of the backing opposite the surface coated with the hydrocolloid composition.

16. The wound dressing of claim 14 wherein the backing extends beyond the periphery of the hydrocolloid composition coating on all sides, and wherein at least a portion of the extended backing surface is coated with a second pressure sensitive adhesive.

17. A method of forming a hydrocolloid composition, the method comprising:
compounding a mixture comprising:
a hydrophobic, unsaturated, elastomeric polymer;
a hydrocolloid absorbent; and
a hydrophilic polymer comprising an unsaturated polymer backbone having polyalkylene ether pendant groups bonded thereto, wherein the polyalkylene ether groups are derived from a hydrophilic polyalkylene oxide-containing compound, wherein the hydrophilic polyalkylene oxide-containing compound comprises ethylene oxide units and optionally co-polymerized propylene oxide units, and wherein the unsaturated polymer backbone comprises one of epoxidized polyubutadiene, polyubutadiene and polyisoprene; and
irradiating the mixture with radiation sufficient to crosslink the hydrophobic and hydrophilic polymers and form a composition with a crosslinked matrix comprising partial unsaturation.

18. The method of claim 17 wherein irradiating the mixture comprises exposing the mixture to a dose of radiation from 5 kGy to 200 kGy.

19. The method of claim 17 wherein the mixture comprises:
a hydrophobic, unsaturated, elastomeric homopolymer;
a tackifier;
a hydrocolloid absorbent selected from the group of a natural hydrocolloid, a semi-synthetic hydrocolloid, a synthetic hydrocolloid, and combinations thereof; and
a hydrophilic polymer comprising an unsaturated polymer backbone having polyalkylene ether groups bonded thereto.

* * * * *

UNITED STATES PATENT AND TRADEMARK OFFICE
CERTIFICATE OF CORRECTION

PATENT NO.         : 10,307,507 B2                                        Page 1 of 2
APPLICATION NO.    : 14/775084
DATED              : June 4, 2019
INVENTOR(S)        : Herbert Chiou It is certified that error appears in the above-identified patent and that said Letters Patent is hereby corrected as shown below:

In the Specification

Column 4
Line 60, Delete "FIG." and insert -- FIGS. --, therefor.

Columns 9-10
Lines 11-23 (approx.),

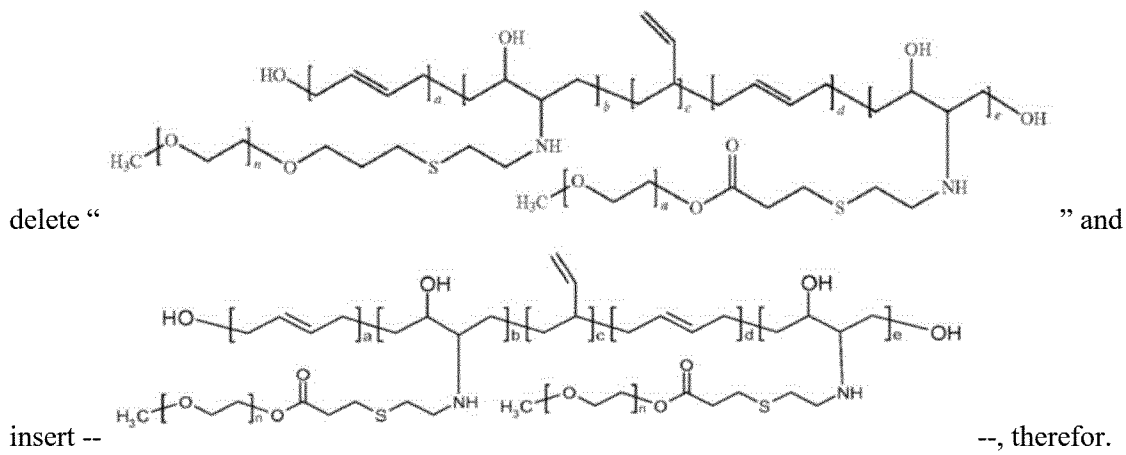

delete "                                                          " and
insert --                                                          --, therefor.

Column 14
Line 35, After "disclosure" insert -- . --.

Column 14
Line 59, Delete "WINTACK" and insert -- WINGTACK --, therefor.

Column 14
Line 59, Delete "NEVTACK" and insert -- NEVTAC --, therefor.

Signed and Sealed this
Third Day of March, 2020

Andrei Iancu
*Director of the United States Patent and Trademark Office*

CERTIFICATE OF CORRECTION (continued)
U.S. Pat. No. 10,307,507 B2

Column 14
Line 62, Delete "(Exxonmobile" and insert -- (Exxonmobil --, therefor.

Column 28
Line 6 (approx.), Delete "(Silvania" and insert -- (Sylvania --, therefor.

Column 29
Line 51 (approx.), Delete "(Silvania" and insert -- (Sylvania --, therefor.

Column 30
Line 49, Delete "(Silvania" and insert -- (Sylvania --, therefor.

Column 31
Line 47 (approx.), Delete "(Silvania" and insert -- (Sylvania --, therefor.

Column 32
Line 12 (approx.), After "sterilization)" insert -- . --.

In the Claims

Column 35
Line 10 (approx.), In Claim 1, delete "polyubutadiene, polyubutadiene" and insert
-- polybutadiene, polybutadiene --, therefor.

Column 36
Line 14 (approx.), In Claim 13, delete "polyubutadiene, polyubutadiene" and insert
-- polybutadiene, polybutadiene --, therefor.

Column 36
Line 48 (approx.), In Claim 17, "polyubutadiene, polyubutadiene" and insert
-- polybutadiene, polybutadiene --, therefor.